(12) United States Patent
Patel

(10) Patent No.: US 11,786,707 B2
(45) Date of Patent: Oct. 17, 2023

(54) INFLATABLE BALLOON OVER CATHETER WITH BYPASS PASSAGEWAY

(71) Applicant: Udayan Patel, Milipitas, CA (US)

(72) Inventor: Udayan Patel, Milipitas, CA (US)

(73) Assignee: Astikay Medical LLC, Milipitas, CA (US)

( * ) Notice: Subject to any disclaimer, the term of this patent is extended or adjusted under 35 U.S.C. 154(b) by 659 days.

(21) Appl. No.: 16/811,699

(22) Filed: Mar. 6, 2020

(65) Prior Publication Data

US 2020/0316350 A1    Oct. 8, 2020

Related U.S. Application Data

(60) Provisional application No. 62/831,076, filed on Apr. 8, 2019.

(51) Int. Cl.
*A61M 25/10* (2013.01)
*A61N 1/32* (2006.01)
*A61F 2/958* (2013.01)

(52) U.S. Cl.
CPC ......... *A61M 25/1002* (2013.01); *A61F 2/958* (2013.01); *A61M 25/104* (2013.01); *A61M 25/1011* (2013.01); *A61N 1/325* (2013.01); *A61N 1/327* (2013.01); *A61M 2025/105* (2013.01); *A61M 2025/1015* (2013.01); *A61M 2025/1079* (2013.01); *A61M 2210/12* (2013.01)

(58) Field of Classification Search
CPC .... A61M 2025/105; A61M 2025/1097; A61M 25/10; A61N 1/327; A61N 1/325
See application file for complete search history.

(56) References Cited

U.S. PATENT DOCUMENTS

| 4,661,094 A | 4/1987 | Simpson |
|---|---|---|
| 4,771,777 A | 9/1988 | Horzewski |
| 4,944,745 A | 7/1990 | Sogard et al. |
| 5,368,566 A | 11/1994 | Crocker |

(Continued)

FOREIGN PATENT DOCUMENTS

| CN | 103654763 | 3/2014 |
|---|---|---|
| WO | 2017142579 | 8/2017 |

OTHER PUBLICATIONS

US Search Authority, International Search Report and Written Report for corresponding application No. PCT/US2020/021509 (dated Jun. 10, 2020).

(Continued)

*Primary Examiner* — Deanna K Hall
(74) *Attorney, Agent, or Firm* — Ulmer & Berne LLP; Brian E. Turung

(57) ABSTRACT

A medical device that delivers therapeutic agent to the tissue within the bodily passageway while simultaneously permitting flow of bodily fluids past the location of treatment. The medical device includes an inflatable balloon and optionally one or more balloon wall openings that are configured to allow fluid in the interior of the inflatable balloon to flow through the inflatable balloon when the inflatable balloon is pressurized by the fluid in the interior of the inflatable balloon. During the inflation of the inflatable balloon at the treatment site, the flow of blood through the blood vessel is maintained across the treatment site by use of one or more bypass passageways in the medical device.

19 Claims, 16 Drawing Sheets

(56) References Cited

U.S. PATENT DOCUMENTS

| | | |
|---|---|---|
| 5,370,617 A | 12/1994 | Sahota |
| 5,498,238 A | 3/1996 | Shapland et al. |
| 5,507,724 A | 4/1996 | Hoffman et al. |
| 5,542,925 A | 8/1996 | Orth |
| 5,573,508 A | 11/1996 | Thornton |
| 5,591,129 A | 1/1997 | Shoup et al. |
| 5,704,908 A | 1/1998 | Hofmann et al. |
| 5,807,306 A | 9/1998 | Shapland et al. |
| 5,989,218 A | 11/1999 | Wasicek |
| 6,068,650 A | 5/2000 | Hofmann et al. |
| 6,398,708 B1 | 6/2002 | Hastings et al. |
| 6,506,180 B1 | 1/2003 | Banning |
| 6,865,416 B2 | 3/2005 | Dev et al. |
| 7,054,685 B2 | 5/2006 | Dimmer et al. |
| 7,395,110 B2 | 1/2008 | Hofmann et al. |
| 8,696,644 B2 | 4/2014 | Baumbach et al. |
| 8,715,230 B2 | 5/2014 | Baumbach et al. |
| 8,801,662 B2 | 8/2014 | Doshi et al. |
| 8,864,787 B2 | 10/2014 | Muni et al. |
| 8,876,472 B2 | 11/2014 | Dijoud et al. |
| 9,039,657 B2 | 5/2015 | Makower et al. |
| 9,314,598 B2 | 4/2016 | Wang |
| 9,452,083 B2 | 9/2016 | Benner et al. |
| 9,629,985 B2 | 4/2017 | Kelly |
| 9,649,478 B2 | 5/2017 | Baumbach et al. |
| 9,649,479 B2 | 5/2017 | Baumbach et al. |
| 9,682,219 B2 | 6/2017 | Venturelli |
| 9,724,495 B2 | 8/2017 | McCullough |
| 9,789,282 B2 | 10/2017 | McKinnon et al. |
| 10,046,092 B2 | 4/2018 | Speck et al. |
| 10,159,821 B2 | 12/2018 | Root et al. |
| 10,207,084 B2 | 2/2019 | Baumbach et al. |
| 10,245,051 B2 | 4/2019 | Spano |
| 2002/0183684 A1 | 12/2002 | Dev et al. |
| 2003/0078539 A1 | 4/2003 | Peterson et al. |
| 2003/0198798 A1 | 10/2003 | Hehrlein et al. |
| 2006/0079923 A1* | 4/2006 | Chhabra .......... A61B 17/12195 606/192 |
| 2006/0190022 A1* | 8/2006 | Beyar .................. A61F 2/958 606/192 |
| 2009/0036830 A1 | 2/2009 | Jablonski et al. |
| 2011/0264039 A1 | 10/2011 | Thielen et al. |
| 2012/0226340 A1 | 6/2012 | Leschinsky |
| 2013/0035637 A1 | 2/2013 | Herweck et al. |
| 2014/0066896 A1 | 3/2014 | Tilson et al. |
| 2015/0230951 A1 | 8/2015 | Al-Saadon |
| 2015/0231386 A1* | 8/2015 | Meyer .................. A61N 1/30 604/503 |
| 2017/0071736 A1 | 3/2017 | Zhu et al. |
| 2017/0151420 A1 | 6/2017 | Laguna |
| 2018/0008763 A1 | 1/2018 | Thomas |

OTHER PUBLICATIONS

China National Search Authority, Search Report for corresponding application CN202080026695.4 (dated Feb. 7, 2023).

European Search Authority, "Partial Supplementary European Search Report" for corresponding application EP 20786540.1 (dated Jan. 2, 2023).

* cited by examiner

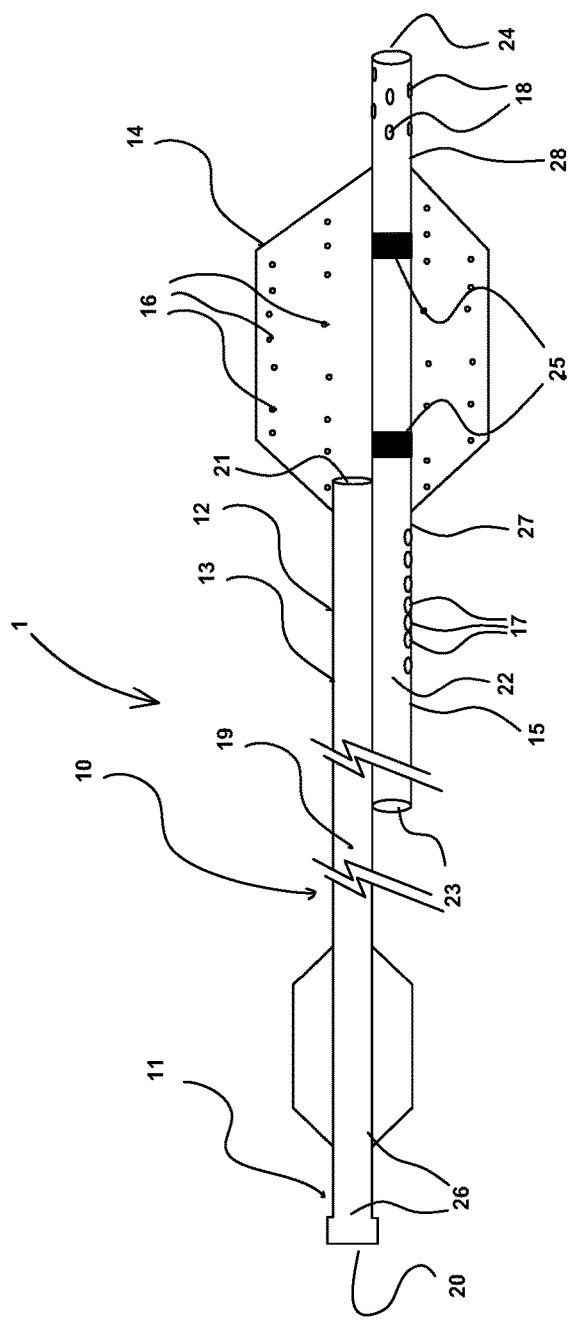
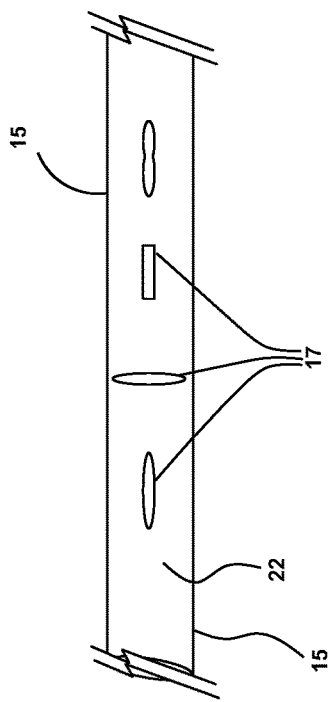
Fig. 1
Fig. 1A

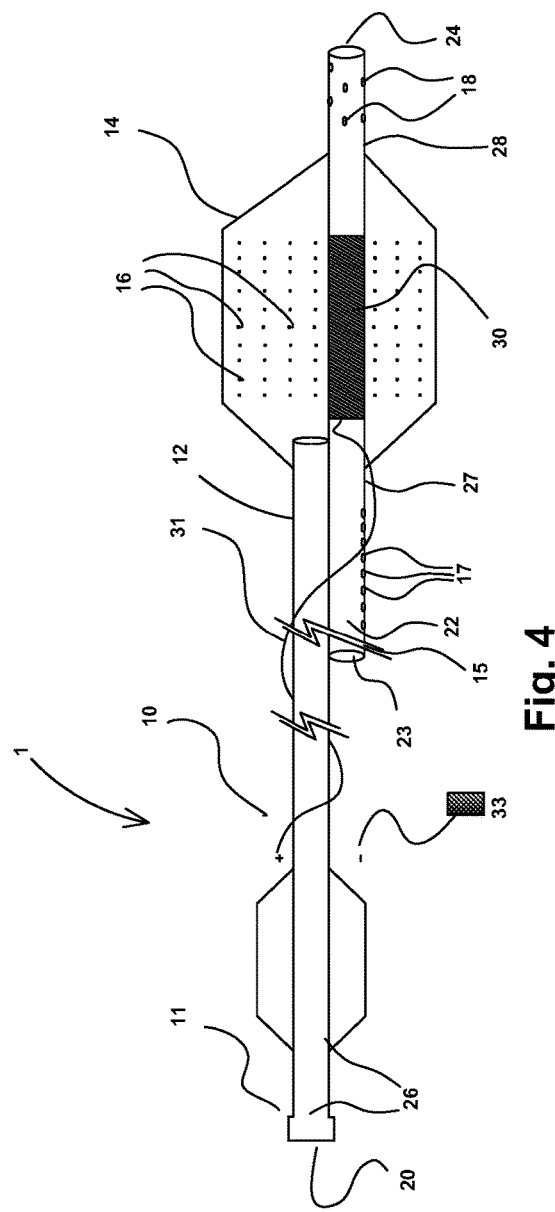
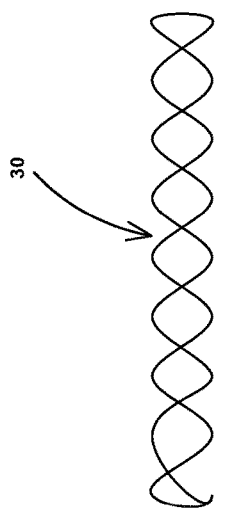
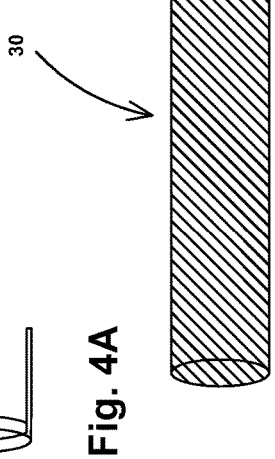
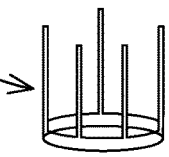
Fig. 4
Fig. 4A
Fig. 4B
Fig. 4C

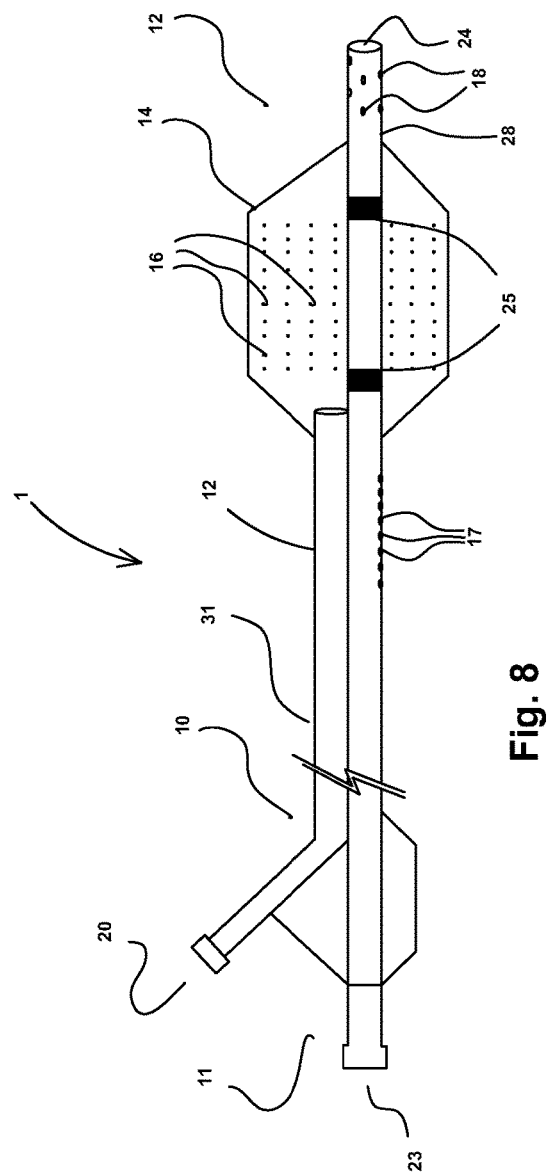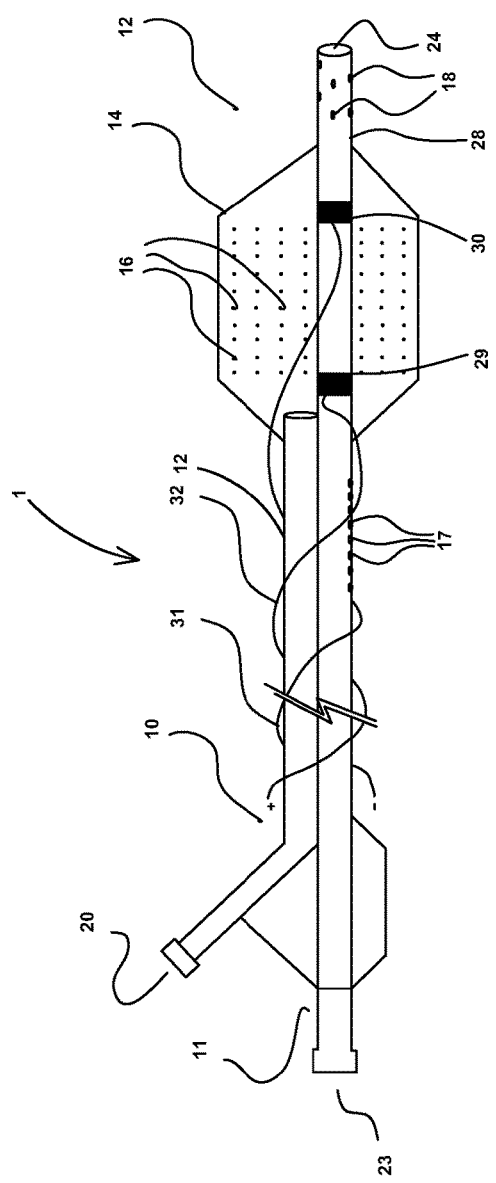

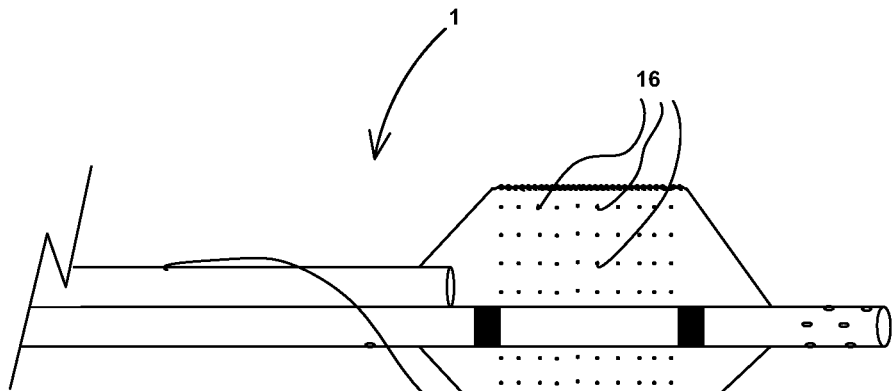
Fig. 11
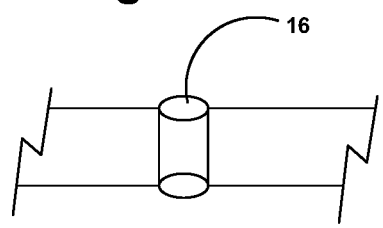
Fig. 11A
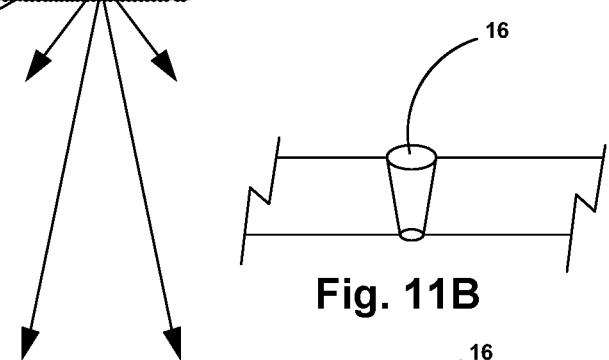
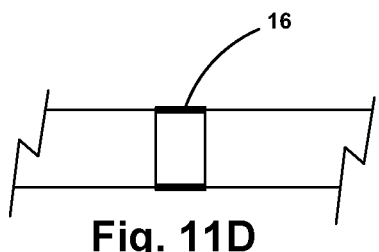
Fig. 11D
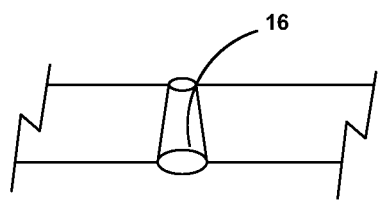
Fig. 11C
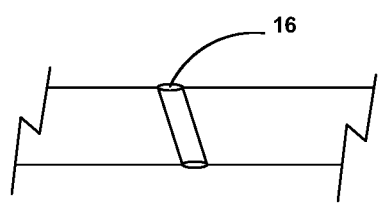
Fig. 11E
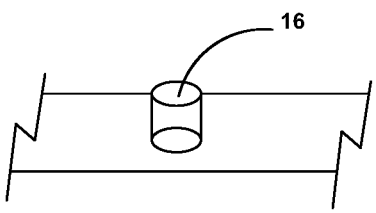
Fig. 11F
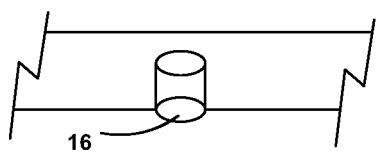
Fig. 11G

INFLATABLE BALLOON OVER CATHETER WITH BYPASS PASSAGEWAY

The present disclosure claims priority on U.S. Provisional Application Ser. No. 62/831,076 filed Apr. 8, 2019, which is incorporated herein by reference.

The present disclosure relates to a medical device that delivers a therapeutic agent (e.g., vasodilator, antithrombosis agent, anti-restenosis drug, etc.) to the tissue within a passageway while simultaneously permitting flow of bodily fluids past the location of treatment. In one non-limiting arrangement, the medical device is configured to deliver a therapeutic agent to a blood vessel where stenosis (i.e., vascular stenosis) may have developed. The medical device includes an inflatable balloon that has the capability to hold high fluid pressure without bursting and is configured to inflate for use in angioplasty procedures. The medical device optionally can be used to facilitate in the delivery of a stent. The medical device can optionally facilitate electroporation and/or iontophoresis for effective delivery of a therapeutic agent within the arterial wall. The inflatable balloon on the medical device is at least partially located at the distal end of the medical device. The inflatable balloon can optionally include one or more pores that are configured to allow fluid (e.g., a fluid that includes one or more therapeutic agents, etc.) in the interior of the inflatable balloon to flow or exude through the one or more pores when the inflatable balloon is partially or fully pressurized by the fluid in the interior of the inflatable balloon. The fluid that flows or is extruded through the one or more pore in the partially or fully inflated inflatable balloon of the medical device contacts the blood vessel wall and then can partially or fully migrates into the tissue of the blood vessel wall by diffusion, which diffusion can optionally be assisted by electroporation and/or iontophoresis. During the inflation of the inflatable balloon of the medical device at the treatment site, the flow of blood through the blood vessel (e.g., vein, artery) is maintained across the treatment site by use of one or more bypass passageways in the medical device. One or more electrodes can optionally be placed on, in, and/or about the inflatable balloon to facilitate electroporation and/or iontophoresis.

BACKGROUND OF THE DISCLOSURE

Stenosis in a blood vessel is caused by the formation of plaque or thrombus on the blood vessel wall. The modern means of relieving stenosis is by angioplasty in which dilatation of the blood vessel is driven by a balloon catheter. In order to maintain the patency of the dilated vessel, a metal scaffold is commonly inserted at the site of the stenosis. In order to prevent restenosis, the stent is commonly provided with a coating of a therapeutic agent or a drug that can inhibit or prevent restenosis. For the therapeutic agent to be effective against restenosis, the therapeutic agent needs to be administered for an extended period, typically about one month. This period of therapeutic agent delivery has been achieved by encapsulating the therapeutic agent between the stent and an excipient. The excipient is typically made of a dissolvable polymeric material. The long-term existence of the stent inside the blood vessel and the excipient has been a cause for late adverse effect in the blood vessel, such as thrombosis. The use of a bioresorbable excipient or an inert polymer such as a fluorinated polymer has reduced the incidence of late thrombus formation; however, the presence of a permanent stent in the blood vessel still results in late adverse effect in the blood vessel.

In more recent inventions, a bioresorbable scaffold has been used; however, due to limitations in mechanical properties of the bioresorbable materials and acidity of the intermediate byproducts, it had not achieved the desired results.

Devices with the therapeutic agent coated over a balloon without a scaffold have been developed in recent years. When the balloon is inflated at the site of treatment, the therapeutic agent is expected to transfer and adhere to the inner surface of the arterial wall. This mode of application of the therapeutic agent is crude in principle because the flow of blood in the blood vessel washes off much or all the therapeutic agent on the blood vessel wall once the balloon is deflated and removed from the blood vessel. The amount of therapeutic agent transferred into the wall of the blood vessel from such devices is uncontrolled and therefore largely variable and inaccurate. When the balloon is fully inflated, the blood flow through the blood vessel is terminated. Depending on the size of the blood vessel, the location of the blood vessel, and the health of the patient, the acceptable time of termination of the blood flow through the blood vessel during treatment of the blood vessel without harming the patient will vary. When treating an artery, the inflation of the balloon will prevent the supply of oxygen and nutrients to the tissues and organs downstream of the inflated balloon. The time of inflation of the balloon is dependent on the tolerance of the tissues to be deprived of the oxygen or nutrients before becoming ischemic. For example, most angioplasty procedures for a coronary artery block the coronary artery by balloon inflation for no more than about 30 seconds in a relatively healthy patient. However, for patients with myocardial infarction, the artery is blocked for no more than about 10 seconds. In neural arteries (e.g., arteries in the brain), the inflation time of the balloon that can be tolerated in an angioplasty procedure is must shorter (e.g., no more than 10-15 seconds). In peripheral arteries, the balloon inflation time for an angioplasty procedure can be a little longer (e.g., up to 30 seconds). In most cases, the inflation time of the inflatable balloon is less than 60 seconds, and typically less than ten seconds for patients with myocardial infarction.

In the short period of time that the inflatable balloon can be inflated in the blood vessel and the short period of time that therapeutic agent can flows from the inflated balloon, the therapeutic agent from the inflated balloon does not have sufficient time to migrate deep within the wall of the blood vessel. Only one therapeutic agent, namely paclitaxel, has proven so far to adhere to the vessel wall for a long enough period of time to be affective. The adherence of paclitaxel to the wall of the blood vessel in a short period of time is due to the high lipophilicity of paclitaxel. However, more recent studies have found that paclitaxel can cause late adverse outcomes in some patients.

Another major drawback of prior art drug-coated balloons is that after the balloon is deflated, the therapeutic agent is washed off the wall of the blood vessel by the resumed blood flow through the blood vessel. In procedures wherein there are multiple short time period inflations of the balloon, the amount of drug available on the outer surface of the balloon after each inflation/deflation will be exponentially diminished. As such, for most therapeutic agents or drugs, this type of procedure (i.e., multiple inflations and deflations of the drug-coated balloon in the region of stenosis) does not result in the desired or required amount of migration of the therapeutic agent into the wall of the blood vessel. For example, a marginally lipophilic drug such as sirolimus that is coated in a balloon requires the balloon to be inflated for longer time periods to allow the sirolimus to adequately diffuse to the medial layer of the blood vessel and not be flushed into the blood stream once the balloon is deflated. The efficiency of the transfer of the therapeutic agent depends on several factors such as a) the ability of the therapeutic agent to detach from the balloon surface, b) adhesion characteristic of the therapeutic agent to the wall of the blood vessel, c) the ability of the therapeutic agent to diffuse through the blood vessel wall, and d) the ability of the therapeutic agent to effectively inhibit restenosis and/or to perform its intended therapeutic function.

In an effort to address the problems associated with the therapeutic agent being washed off the blood vessel wall after deflation of the balloon, the therapeutic agents or drugs have been coated or encapsulated in a lipophilic excipient that adheres to the wall of the blood vessel more readily than the therapeutic agent. However, not all therapeutic agents can be successfully coated or encapsulated in a lipophilic excipient. Also, the need to coat or encapsulate the therapeutic agent adds a level of complexity to the treatment of stenosis that can cause undesired long-term clinical outcomes and can also or alternatively limit the choice of compatible therapeutic agents used in the treatment.

Attempts have been made to use a needle to navigate through the blood vessel and puncture the blood vessel wall to inject a therapeutic agent into the blood vessel wall. When using such a device, a point of vessel injury will be induced by the needle, which injury can cause inflammation and related undesired side effects.

Another device that has been used consists of an ultrasonic aid to quickly infuse the therapeutic agent into the blood vessel wall; however, such treatment has proven ineffective mostly due to limitation to duration of treatment. Other attempts to quickly infuse the therapeutic agent into the blood vessel wall use the technique of electroporation or iontophoresis; however, these techniques have also failed due to either excessive injury to the blood vessel wall during very high voltage electrical discharge required for effective transfer of drug into the tissue of the blood vessel within the short duration of balloon inflation as tolerated by the organs.

Another attempt to a supply therapeutic agent into the blood vessel wall during the inflation of the balloon included the use of holes in the balloon through which the therapeutic agent could be discharged from the interior of the inflated balloon into the blood vessel wall. The drawback for such a device is two-fold, namely 1) the limitation of duration time of treatment since the balloon could only be inflated for short time periods, and 2) the ability to pressurize and fully inflate the balloon and also be able to be appose to the outer surface of the inflated balloon against the blood vessel wall so as to deliver the therapeutic agent into the blood vessel wall. In such devices, a second balloon is positioned inside the porous balloon to enable the porous balloon to fully appose against the blood vessel wall; however, the use of two inflatable balloons in the device increases the bulkiness and size of the device thereby making the device more difficult to navigate in the blood vessel to the area of stenosis.

Due to the limitation in treatment time when using an inflatable balloon for treatment of stenosis, the choice of therapeutic agents or drugs is limited; thus, the drug-coated balloons and other devices that transfer therapeutic agent superficially to the wall of the blood vessel have not been effective.

In view of the current state of the art of inflatable balloons for use in the treatment of stenosis, there is a need for a medical device that includes an inflatable balloon that is configured to effectively deliver therapeutic agent to the tissue of the blood vessel.

SUMMARY OF THE DISCLOSURE

The present disclosure is directed to a medical device and method of treating stenosis by use of an inflatable balloon, wherein the medical device and method overcome the past deficiencies and limitations of prior art inflatable balloons for use in the treatment of stenosis. The medical device and method of treating stenosis by use of an inflatable balloon in accordance with the present disclosure enables therapeutic agent to be effectively transferred to the tissue of the blood vessel without preventing the flow of blood through the blood vessel while the balloon is inflated. Additionally, the medical device and method in accordance with the present disclosure optionally promotes diffusion of the therapeutic agent into the blood vessel wall without puncturing the blood vessel wall. Additionally, the medical device and method in accordance with the present disclosure provides flexibility to provide the blood vessel wall with a therapeutic agent that is either encapsulated or non-encapsulated, and to optionally continue to provide the blood vessel wall with the therapeutic agent until a desired saturation point of the therapeutic agent within the blood vessel wall is achieved while simultaneously permitting blood flow past the site of treatment. The medical device and method in accordance with the present disclosure addresses the shortfalls of current inflatable balloon devices for the treatment of stenosis and fulfills a medical need by providing the caregiver a flexibility in targeted dose treatment of each patient for a better outcome.

In one non-limiting aspect of the present disclosure, the medical device and method is directed, but not limited, to treatment of a diseased blood vessel by delivering a therapeutic agent (hereinafter collectively referred to as a 'therapeutic agent') while simultaneously facilitating flow of bodily fluids past the point of treatment.

In accordance with another and/or alternative non-limiting aspect of the present disclosure, the medical device includes a catheter body wherein the distal end is in communication with an inflatable balloon via an inflation lumen. The medical device includes one or more bypass passageways that allow fluid in the blood vessel to move past the inflatable balloon when the inflatable balloon is in a partially or fully inflated state. The one or more bypass passageway can be formed by 1) the guidewire passageway (e.g., guidewire lumen) that is used by the guidewire, and/or 2) a second passageway separate from the guidewire passageway. When the guidewire passageway is used to fully form at least one of the bypass passageways, the guidewire passageway is generally configured to fully pass through the inflatable balloon. The one or more bypass passageways include one or more openings located prior to the location of the inflatable balloon (located prior to the posterior end of the inflatable balloon) and one or more openings located after the location of the inflatable balloon (located after the anterior end of the inflatable balloon), and wherein the one or more openings are located in the blood vessel when the inflatable balloon is positioned at the treatment site in the blood vessel. The number and size of the one or more openings in the one or more bypass passageways are selected so that at least 5 vol. % of the pretreatment fluid flow rate through the blood vessel (e.g., pretreatment fluid flow rate is the flow rate of fluid through the blood vessel prior to the medical device being inserted into the treatment area of the blood vessel) is maintained when the inflatable balloon is 90-100% inflated (and all values and ranges therebetween) in the blood vessel. In one non-limiting embodiment, the number and size of the one or more openings in the one or more bypass passageways are selected so that at least 10 vol. % (and all values and ranges therebetween) of the pretreatment fluid flow rate through the blood vessel is maintained when the inflatable balloon is 90-100% inflated (and all values and ranges therebetween) in the blood vessel. In another non-limiting embodiment, the number and size of the one or more openings in the one or more bypass passageways are selected so that at least 20 vol. % of the pretreatment fluid flow rate through the blood vessel is maintained when the inflatable balloon is 90-100% inflated in the blood vessel. In another non-limiting embodiment, the number and size of the one or more openings in the one or more bypass passageways are selected so that at least 40 vol. % of the pretreatment fluid flow rate through the blood vessel is maintained when the inflatable balloon is 90-100% inflated in the blood vessel. In another non-limiting embodiment, the number and size of the one or more openings in the one or more bypass passageways are selected so that at least 50 vol. % of the pretreatment fluid flow rate through the blood vessel is maintained when the inflatable balloon is 90-100% inflated in the blood vessel. In another non-limiting embodiment, the number and size of the one or more openings in the one or more bypass passageways are selected so that at least 60 vol. % of the pretreatment fluid flow rate through the blood vessel is maintained when the inflatable balloon is 90-100% inflated in the blood vessel. In one non-limiting embodiment, the medical device includes a single bypass passageway. In another non-limiting embodiment, the medical device includes two or more bypass passageways. In another non-limiting embodiment, when the inflatable balloon is 90-100% inflated (and all values and ranges therebetween) at the treatment site in the blood vessel, at least 50 vol. % of the fluid that flows through the treatment site and bypasses the inflated inflatable balloon of the medical device flows through the one or more bypass passageways. In another non-limiting embodiment, when the inflatable balloon is 90-100% inflated at the treatment site in the blood vessel, 50-100 vol. % of the fluid (and all values and ranges therebetween) that flows through the treatment site and bypasses the inflated inflatable balloon of the medical device flows through the one or more bypass passageways. In another non-limiting embodiment, when the inflatable balloon is 90-100% inflated at the treatment site in the blood vessel, at least 60 vol. % of the fluid that flows through the treatment site and bypasses the inflated inflatable balloon of the medical device flows through the one or more bypass passageways. In another non-limiting embodiment, when the inflatable balloon is 90-100% inflated at the treatment site in the blood vessel, at least 80 vol. % of the fluid that flows through the treatment site and bypasses the inflated inflatable balloon of the medical device flows through the one or more bypass passageways. In another non-limiting embodiment, when the inflatable balloon is 90-100% inflated at the treatment site in the blood vessel, 100 vol. % of the fluid that flows through the treatment site and bypasses the inflated inflatable balloon of the medical device flows through the one or more bypass passageways.

In accordance with another and/or alternative non-limiting aspect of the present disclosure, the medical device includes a secondary passageway (which is not used with a guidewire) to fully form a bypass passageway. In one non-limiting arrangement of this non-limiting embodiment, the secondary passageway is configured to pass fully through the inflatable balloon and the secondary passageway has one or more openings that are located at or prior to the posterior end of the inflatable balloon and also has one or more openings that are located at or after the anterior end of the inflatable balloon. Generally, the one or more openings on the secondary passageway located prior to the posterior end of the inflatable balloon are located 0-20 in. (and all values and ranges therebetween) of the anterior or proximal end of the inflatable balloon, and typically about 0-5 in. of the anterior or proximal end of the inflatable balloon, and more typically 0-2 in. of the anterior or proximal end of the inflatable balloon. Generally, the one or more openings on the secondary passageway located after to the posterior or distal end of the inflatable balloon are located 0-5 in. (and all values and ranges therebetween) of the posterior or distal end of the inflatable balloon, and typically about 0-0.5 in. of the posterior or distal end of the inflatable balloon, and more typically 0-0.2 in. of the posterior or distal end of the inflatable balloon.

In accordance with another and/or alternative non-limiting aspect of the present disclosure, the medical device includes a secondary passageway that is used to partially form a bypass passageway. In one non-limiting arrangement of this non-limiting embodiment, the secondary passageway is configured to be connected to another passageway (e.g., guidewire passageway, therapeutic fluid passageway, balloon inflation passageway, etc.) such that the secondary passageway forms a portion of the bypass passageway and the other passageway forms another portion of the bypass passageway. For example, a first end of the secondary passageway can be fluidly connected to the guidewire passageway (however, it will be understood that the other passageways such as therapeutic fluid passageway, balloon inflation passageway can be used) and the second end of the secondary passageway can extend outwardly from the posterior or distal end of the inflatable balloon. In such an arrangement, the second end of the secondary passageway that extends outwardly from the posterior or distal end of the inflatable balloon includes one or more openings. Also, in this arrangement, the guidewire passageway includes one or more fluid openings that are located prior to the anterior or proximal end of the inflatable balloon (e.g., the one or more fluid openings are spaced from the first end of the guidewire passageway and are located in the guidewire passageway such that fluid in the blood vessel can flow into the guidewire passageway when the inflatable balloon has been positioned at the treatment site). In this non-limiting arrangement, the first end of the secondary passageway is generally connected to the guidewire passageway at a location that is at or after the location of the one or more fluid openings in the guidewire passageway. Generally, the one or more fluid openings on the guidewire passageway are located 0-20 in. (and all values and ranges therebetween) of the anterior or proximal end of the inflatable balloon, and typically about 0-5 in. of the anterior or proximal end of the inflatable balloon, and more typically 0-2 in. of the anterior or proximal end of the inflatable balloon. Generally, the one or more openings on the secondary passageway located after to the posterior or distal end of the inflatable balloon are located 0-5 in. (and all values and ranges therebetween) of the posterior or distal end of the inflatable balloon, and typically about 0-0.5 in. of the posterior or distal end of the inflatable balloon, and more typically 0-0.2 in. of the posterior or distal end of the inflatable balloon.

In accordance with another and/or alternative non-limiting aspect of the present disclosure, the medical device includes a guidewire passageway that is used to fully form a bypass passageway. In one non-limiting arrangement of this non-limiting embodiment, the guidewire passageway is configured to pass fully through the inflatable balloon and the guidewire passageway has one or more fluid openings (e.g., the one or more fluid openings are spaced from the first end of the guidewire passageway and are located in the guidewire passageway such that fluid in the blood vessel can flow into the guidewire passageway when the inflatable balloon has been positioned at the treatment site) that are located at or prior to the anterior or proximal end of the inflatable balloon and also has one or more fluid openings that are located at or after the anterior end of the inflatable balloon. Generally, the one or more fluid openings on the guidewire passageway located prior to the posterior end of the inflatable balloon are located within 0-20 in. (and all values and ranges therebetween) of the posterior end of the inflatable balloon, and typically about 0-5 in. of the posterior end of the inflatable balloon, and more typically 0-2 in. of the posterior end of the inflatable balloon. Generally, the one or more fluid openings on the secondary passageway located after to the anterior end of the inflatable balloon are located within 0-20 in. (and all values and ranges therebetween) of the anterior end of the inflatable balloon, and typically about 0-5 in. of the anterior end of the inflatable balloon, and more typically 0-2 in. of the anterior end of the inflatable balloon.

In accordance with another and/or alternative non-limiting aspect of the present disclosure, the medical device optionally includes one or more radiopaque markers. The one or more radiopaque markers facilitate in positioning the medical device at the treatment site within a blood vessel. In one non-limiting embodiment, the one or more radiopaque markers are located inside the inflatable balloon. In this non-limiting arrangement, the radiopaque markers radiopaque markers are located on the inflation passageway (e.g., inflation lumen) or the guidewire passageway (e.g., guidewire lumen) that partially or fully passes through the inflation balloon. As can be appreciated, one or more radiopaque markers can be located outside the inflation balloon.

In accordance with another and/or alternative non-limiting aspect of the present disclosure, the inflatable balloon of the medical device optionally includes one or more balloon wall openings that are sized to allow the passage of a therapeutic material (e.g., one or more therapeutic agents [e.g., vasodilator, antithrombosis agent, anti-restenosis drug, etc.], one or more coated therapeutic agents (e.g., coated or encapsulated therapeutic agent using an excipient or other type of coating, a solution of one or more therapeutic agents and/or coated therapeutic agents, etc.) to pass through the inflatable balloon wall. The number and size of the one or more balloon wall openings are selected to enable the inflatable balloon to be fully inflated and hold a desired internal pressure in the inflatable balloon (e.g., 1-20 Atm. and all values and ranges therebetween). As such, the number and size of the one or more balloon wall openings allows for the desired flowrate of therapeutic material from the interior of the inflated inflatable balloon, through the wall of the inflatable balloon, then on the wall of the blood vessel while also holding a desired internal inflation pressure of the inflatable balloon so as to properly expand the blood vessel at the treatment the area of stenosis in the blood vessel. When the inflatable balloon optionally includes one or more balloon wall openings, the maximum internal pressure in the inflatable balloon (when inflated) is dependent on the size of the one or more balloon wall openings, the number of balloon wall openings, and the viscosity of the fluid that is used to inflate the inflatable balloon. For example, an inflatable balloon with 120 equally spaced balloon wall opening that all have a 1 micron diameter will allow the inflatable balloon to be inflated and hold an internal pressure of about 6 Atm. when using an inflation fluid of a 50:50 mixture of contrast agent and saline having a viscosity of 5 cps at 77°. The viscosity of various fluids used to inflate the inflatable balloon can vary. For example, a 100% saline solution (14%-20% NaCl solution) has a viscosity of about 1.3-1.6 cps at 77°. A 50/50 saline solution-therapeutic agent has a viscosity of about 1.3-3 cps at 77°. A 100% solution of contrast agent or radiopaque fluid has a viscosity of about 5-12 cps at 77°. As can be appreciated, different sized balloon wall openings, a different number of balloon wall openings, and/or solution viscosity can be used to inflate the inflatable balloon to different internal pressures. The size of the one or more balloon wall openings and pattern of the balloon wall openings on the inflatable balloon can optionally be selected based on the size and configuration of the therapeutic material and/or the fluid used to inflate the inflatable balloon. Generally, the inflatable balloon is configured to be inflated to maintain an internal pressure of 1-30 Atm. (and all values and ranges therebetween), typically 2-20 Atm, and more typically about 3-12 Atm. The one or more balloon wall openings in the inflatable balloon can be optionally formed by a sharp needle, a laser, a hole punch, or similar technique known in the industry for making micropores. In another non-limiting embodiment, one or more of the balloon wall openings can optionally be formed by balloon wall pores that have been partially formed in the balloon wall (e.g., pores create a thinner wall thickness in the inflatable balloon wall), but which balloon wall pores do not fully penetrate the balloon wall until after the first inflation of the inflatable balloon. The balloon wall pores are configured to only form openings through the balloon wall after the inflatable balloon has been inflated and the stretching of the balloon wall during inflation and/or the internal pressure within the inflatable balloon during inflation causes the balloon wall pores to rupture or open to thereby form a balloon wall openings in the balloon wall. In another non-limiting embodiment, one or more of the balloon wall openings can optionally be formed by using a porous balloon material, such as an open cell foam material. When the inflatable balloon optionally includes one or more balloon wall openings, the rate at which the therapeutic material flows or extrudes through the one or more balloon wall openings is a function of the internal pressure of the inflatable balloon, the viscosity of the fluid in the inflatable balloon, the wall thickness of the inflatable balloon, the size of the one or more balloon wall openings, the number of balloon wall openings, the distribution pattern of the balloon wall openings on the inflatable balloon, the size of any the particles (e.g., therapeutic material particles, radiopaque particles or fluid (e.g., iodine, barium, diatrizoates, iohexol, iopamidol, iothalamate, ioversol, ioxaglate, metrizamide, etc.), dye or coloring agent particles, salt particles, particles of biological material, etc.) in the fluid in the inflatable balloon, the amount of force exerted by the blood vessel wall on the inflated inflatable balloon surface, and the overexpansion of the blood vessel. Generally, the therapeutic material is flowed or extruded through the one or more balloon wall openings by 1) maintaining a generally constant internal pressure within the inflatable balloon and/or 2) keeping a generally constant volume of fluid/therapeutic material flowing out of the inflatable balloon. When the fluid/therapeutic material flows out of the inflatable balloon at a high pressure (e.g., at least 16 Atm.) and/or at high rate of speed through the one or more balloon wall openings (e.g., at least 0.25 mm/sec.), the fluid/therapeutic material flowing out of the inflatable balloon fluid can be injected deep into the blood vessel wall and into the medial or outer layers of the blood vessel. As can be appreciated, the speed of the fluid/therapeutic material through the one or more balloon wall openings of the inflatable balloon can be 0.01 mm/sec. or more, and typically 0.01-1 mm/sec. (and all values and ranges therebetween).

In accordance with another and/or alternative non-limiting aspect of the present disclosure, the inflatable balloon is optionally foldable into smaller profile to facilitate in the insertion of the medical device at the treatment area in the blood vessel. The folded inflatable balloon can be configured to unfold and inflate at the treatment site.

In accordance with another and/or alternative non-limiting aspect of the present disclosure, the medical device is configured to allow blood to flow through the medical device that is located at the treatment site in the blood vessel when the inflatable balloon is fully inflated. While the inflatable balloon is inflated at the treatment site in the blood vessel, therapeutic agent can optionally be applied to the wall of the blood vessel that is closely adjacent to or in contact with the blood vessel wall. Such therapeutic agent can optionally be applied to the wall of the blood vessel by 1) coating the outer surface of the inflatable balloon with one or more therapeutic agents, 2) coating the outer surface of the inflatable balloon with one or more coated or encapsulated therapeutic agents, and/or 3) causing therapeutic material (e.g., one or more therapeutic agents [e.g., vasodilator, antithrombosis agent, anti-restenosis drug, etc.], one or more coated therapeutic agents (e.g., coated or encapsulated therapeutic agent using an excipient or other type of coating, a solution of one or more therapeutic agents and/or coated therapeutic agents, etc.) to flow or pass through one or more balloon wall openings in the inflated inflatable balloon.

In accordance with another and/or alternative non-limiting aspect of the present disclosure, the medical device is configured to be used in conjunction with other devices such, but not limited to, a guide catheter or the guide sheath, a guide wire, a syringe, and/or a balloon pressurization device.

In accordance with another and/or alternative non-limiting aspect of the present disclosure, the medical device can optionally include one or more radiopaque markers to ensure proper placement of the inflated balloon in the blood vessel. When one or more radiopaque markers are included on the medical device, the use of a radiopaque liquid can be eliminated.

In accordance with another and/or alternative non-limiting aspect of the present disclosure, a dye can optionally be mixed with the therapeutic material and be used as fluid to partially or fully inflate the inflatable balloon.

In accordance with another and/or alternative non-limiting aspect of the present disclosure, a gaseous drug carrier can optionally be used to partially or fully inflate the inflatable balloon and optionally be used to deliver therapeutic material to the inflatable balloon.

In accordance with another and/or alternative non-limiting aspect of the present disclosure, the medical device can optionally include an electrical field-generating element. The electrical field-generating element generally includes two electrodes. Generally, the two electrodes create an electrical field. Generally, the two electrodes are located near the two ends of the inflatable balloon. The electrodes can be located within the inflatable balloon and/or outside the inflatable balloon. One electrode is an anode and the other electrode is the cathode. The two electrodes are generally extended to the proximal end of the catheter by two electrically conducting wires such that they do not short the circuit. During the inflation of the inflatable balloon, pressurization of the inflatable balloon, and/or optional stent deployment in the treatment area of the balloon vessel, an electrical current can be flowed through the two electrodes. The tissue between the two electrodes is charged by the current flowing through the two electrodes to cause an effect known as electroporation. Electroporation can be used to facilitate the transferring of therapeutic material deep into the blood vessel wall tissue. The electroporation treatment, when optionally used with the medical device, can be used while maintaining blood flow through and past the treatment site in the blood vessel via the bypass passageway in the medical device.

In accordance with another and/or alternative non-limiting aspect of the present disclosure, the medical device can optionally include a single electrode that acts as an anode. During the procedure to treat a site in a blood vessel using the medical device, a cathode plate can optionally be placed on the patient's body close to the treatment site. During the treatment of the site by the medical device, an electrical current can optionally be passed through the anode to create electroporation. The anode can be in the form of an electrode located within the inflatable balloon and/or outside the inflatable balloon, or optionally can be the metallic stent, when such a stent is used.

In accordance with another and/or alternative non-limiting aspect of the present disclosure, the medical device can optionally include a side branch passageway that is formed off of the bypass passageway. The side branch passageway can be configured to provide blood at a location between the proximal and distal ends of the inflatable balloon. One non-limiting arrangement, the side branch passageway forms an opening in the wall of the inflatable balloon between the proximal and distal ends of the inflatable balloon. The side branch passageway provides passage for blood flow to the wall of the blood vessel during the inflation of the inflatable balloon.

In accordance with another and/or alternative non-limiting aspect of the present disclosure, the medical device can optionally include a second inflatable balloon that is positioned adjacent to the first inflatable balloon (e.g., the inflatable balloon on the medical device that has been previously described above) or spaced from the first inflatable balloon. When the medical device includes first and second balloons, the first end of the bypass passageway is configured to include one or more openings at or prior to the proximal end of the first inflatable balloon and the second end of the bypass passageway is configured to include one or more openings at or after the distal end of the second inflatable balloon. The second inflatable balloon can optionally include radiopaque markers as described above with respect to the first inflatable balloon, which radiopaque markers can be used to ensure proper placement of the first and/or second inflatable balloon in the blood vessel. When the medical device includes first and second inflatable balloons, an auxiliary balloon passageway can optionally be used to fluidly connected the first and second inflatable balloons. Such auxiliary balloon passageway allows fluid being used to inflate the first inflatable balloon to also be used to inflate the second inflatable balloon. In such an arrangement, both the first and second inflatable balloons can simultaneously be inflated. The first and/or second inflatable balloon can optionally include one more balloon wall openings to allow therapeutic material to flow or extrude from the first and/or second inflatable balloons onto the blood vessel wall as previously described above with respect to the first inflatable balloon. The first and/or second inflatable balloon can optionally include one or more electrodes so as to perform an electroporation treatment as previously described above with respect to the first inflatable balloon.

In accordance with another and/or alternative non-limiting aspect of the present disclosure, a non-limiting method for using the medical device is as follows: 1) the guide catheter is first introduced into the body and into the vasculature and navigated to the close proximity of the treatment site, 2) a guide wire is then navigated through the guide catheter and extended past the treatment site, 3) the medical device in accordance with the present disclosure is then introduced over the guide wire and through the guide catheter and navigated to the treatment site such that the inflatable balloon of the medical device is placed across the treatment site, and optional markers on the medical device can be used in the proper positioning of the medical device at the treatment site, 4) the inflatable balloon is then pressurized with a fluid, which fluid can optionally include a therapeutic material (e.g., one or more therapeutic agents [e.g., vasodilator, antithrombosis agent, anti-restenosis drug, etc.], one or more coated therapeutic agents (e.g., coated or encapsulated therapeutic agent using an excipient or other type of coating, a solution of one or more therapeutic agents and/or coated therapeutic agents, etc.), 5) as the inflatable balloon in inflated, the inflatable balloon expands and the outer wall of the inflatable balloon apposes against the wall of the blood vessel at the treatment site, and the expansion of the inflatable balloon can optionally increase the cross-sectional area of the opening in the treatment area of the blood vessel, 6) when the inflatable balloon is fully deployed (e.g., fully inflated at the treatment area), blood flow about the inflatable balloon is substantially or fully terminated except for the continued flow of blood about the inflated inflatable balloon via the one or more bypass passageways in the medical device, 7) therapeutic material can optionally be applied to the wall of the blood vessel that is closely adjacent to or in contact with the inflatable balloon at the treatment site by a) flowing therapeutic material into the interior of the inflatable balloon and causing the therapeutic material (e.g., one or more therapeutic agents [e.g., vasodilator, antithrombosis agent, anti-restenosis drug, etc.], one or more coated therapeutic agents (e.g., coated or encapsulated therapeutic agent using an excipient or other type of coating, a solution of one or more therapeutic agents and/or coated therapeutic agents, etc.) to flow or pass through one or more balloon wall openings in the inflated inflatable balloon, b) coating the outer surface of the inflatable balloon with one or more therapeutic agents, and/or c) coating the outer surface of the inflatable balloon with one or more coated or encapsulated therapeutic agents, 8) the inflatable balloon can remain inflated at the treatment site as long as needed for proper treatment of the blood vessel (e.g., allow sufficient time for one or more therapeutic agents to infuse in desired quantities into the wall of the blood vessel, etc.), and 9) once the treatment of the blood vessel is complete, the inflatable balloon can be partially or fully deflated, and the inflatable balloon, guide wire, guide wire catheter, etc., can be removed from the blood vessel. In one optional additional step, prior to the inflatable balloon, guide wire, guide wire catheter, etc., being removed from the blood vessel, the inflatable balloon can be partially or fully deflated at the treatment site and the fluid containing the therapeutic material can optionally be retrieved from the inflatable balloon fluid and, thereafter, the balloon can be filled with a high viscosity solution, which solution has particles that resist or cannot pass through the one or more balloon wall openings so that the inflatable balloon can then be inflated to a higher pressure than could be used when the inflatable balloon was inflated by a solution that included the therapeutic material. A high viscosity solution is defined as a solution having a viscosity of 2.5 cps or greater at 77°. Generally, the average particle size of the particles in a fluid that is not a high viscosity solution will be less than 50% of the size of the opening in the balloon wall openings when the inflatable balloon is inflated 75-100% (and all values an ranges therebetween) at the treatment site in the blood vessel so that the non-high viscosity solution will pass unobstructed through the balloon wall openings when the inflatable balloon is inflated 75-100%. In one particular non-limiting embodiment, the non-high viscosity solution has a viscosity of less than 2.4 cps at 77° F., and the particles in the non-high viscosity solution have an average particle size of less than 50% of the size of the opening in the balloon wall openings when the inflatable balloon is inflated 7%-100%. In another particular non-limiting embodiment, the non-high viscosity solution has a viscosity of 0.9-2.4 cps at 77° F. (and all values and ranges therebetween), and the particles in the non-high viscosity solution have an average particle size of less than 45% of the size of the opening in the balloon wall openings when the inflatable balloon is inflated 75-100%. The high viscosity solution can optionally include a dye, contract agent, and/or radiopaque particles. For example, when the inflatable balloon is inflated with a solution of saline solution and therapeutic material (which is a non-high viscosity solution) such solution can be used to inflate the inflatable balloon to an internal pressure of up to 6-8 Atm. Generally, a 0.1 wt. % solution of therapeutic agent in a saline solution has a viscosity of no more than about 2 cps at 77° F. Such a solution can have a flowrate through the balloon wall openings when the inflatable balloon is inflated with such solution of a rate of 0.05-0.25 mm/sec. Generally, an inflatable balloon having balloon wall openings cannot be inflated to internal pressures above 8 Atm. when using a non-high viscosity solution to inflate the inflatable balloon. As such, if the inflatable balloon needs to be inflated at higher internal pressures to properly treat the blood vessel at the treatment site, a high viscosity solution is used to inflate the inflatable balloon to such higher internal pressures. The high viscosity solution includes particles that resist or cannot pass through the one or more balloon wall openings, thus enable greater internal pressures to be obtained. Generally, the average size of the particles in the high viscosity solution is 50-100+% the average size of the one or more balloon wall openings (and all values and ranges therebetween) when the inflatable balloon is inflated 75%-100% at the treatment site in the blood vessel (and all values and ranges therebetween), typically the average size of the particles in the high viscosity solution is 75-100+% the average size of the one or more balloon wall openings when the inflatable balloon is inflated 75-100% at the treatment site in the blood vessel, and more typically the average size of the particles in the high viscosity solution is 80-100+% the average size of the one or more balloon wall openings when the inflatable balloon is fully inflated at the treatment site in the blood vessel. The inflation of the inflatable balloon at higher internal pressures expands the opening at the treatment area to a desired size prior to the removal of the inflatable balloon form the treatment site. As can be appreciated, the therapeutic material does not need to be partially or fully withdrawn from the inflatable balloon prior to inserting a high viscosity solution into the inflatable balloon to inflate the inflatable balloon. If the therapeutic material is not partially or fully withdrawn from the inflatable balloon prior to inserting the high viscosity solution into the inflatable balloon, the high viscosity solution can be used to 1) partially or fully plug the one or more balloon wall openings to partially or fully prevent further therapeutic material from passing through the balloon wall openings, or 2) partially plug the one or more balloon wall openings to require higher internal pressures to allow the therapeutic material to pass through the balloon wall openings. Generally, the high viscosity solution is formulated to be able to inflate an inflatable balloon having a plurality of balloon wall openings to an internal pressure that is at least 20% greater that the internal pressure of the balloon being inflated by a saline solution of NaCl having a viscosity of 1.6 cps at 77°. Typically, the high viscosity solution is formulated so that the high viscosity solution is able to inflate an inflatable balloon having a plurality of balloon wall openings to an internal pressure that is at least 40% greater that the internal pressure of the balloon being inflated by a saline solution of NaCl having a viscosity of 1.6 cps at 77°. More typically, the high viscosity solution is formulated to inflate an inflatable balloon having a plurality of balloon wall openings to an internal pressure that is at least 50% greater that the internal pressure of the balloon being inflated by a saline solution of NaCl having a viscosity of 1.6 cps at 77°.

In another optional method or procedure step, the inflatable balloon can optionally be inflated by a fluid that is or includes a radiopaque liquid or contrast agent. Generally, such a fluid is a high viscosity solution. A therapeutic material can optionally be included in the radiopaque liquid. The contrast agent is generally deemed harmless to the blood vessel. The radiopaque liquid is typically used for its radiopacity that allows the operator to ensure to locate the disease in the blood vessel. The radiopaque liquid can also be used to partially or fully seal or plug the one or more balloon wall openings; however, this is not required. In one non-limiting method or procedure that includes the use of radiopaque liquid, 1) the inflatable balloon is inserted at the treatment site, 2) the inflatable balloon is partially or fully inflated with a fluid that is or includes a radiopaque liquid, 3) the position of the inflatable balloon at the treatment site is verified and/or adjusted based on the viewing of the radiopaque liquid in the partially or fully inflated inflatable balloon, 4) the radiopaque liquid is optionally fully or partially withdrawn from the inflatable balloon after the inflatable balloon has been verified to be in the proper position in the treatment site, 5) the inflatable balloon is again inflated if the inflatable balloon was partially or fully deflated when the radiopaque liquid was optionally withdrawn from the inflatable balloon, and 6) therapeutic material is optionally inserted into the interior of the inflated inflatable balloon such that the therapeutic material can optionally be applied to the wall of the blood vessel by the therapeutic material flowing or extruding through the wall of the inflatable balloon.

In another optional method or procedure step, when greater flow of blood is desired across the site of treatment during the inflation of the inflatable balloon and the guidewire catheter is used to partially or fully from a bypass passageway, the guide wire can optionally be retracted back to a point such that the distal end of the guide wire resides proximal to the most proximal opening in the bypass passageway such that the guide wire is not located between any of the openings in the bypass passageway. The ability of the medical device in accordance with the present disclosure to allow the continued flow of blood across the treatment site while the inflatable balloon is inflated allows for prolonged periods of treatment without asphyxiation of vital organs.

In accordance with another and/or alternative non-limiting aspect of the present disclosure, the medical device can optionally include a stent. The stent can be mounted on the inflatable balloon and delivered to the treatment site where the stent can be expanded and deployed at the treatment site when the inflatable balloon is inflated at the treatment site. During the stent deployment, therapeutic material can optionally be applied to the wall of the blood vessel by 1) the therapeutic material being coated on the stent, 2) the therapeutic material being coated on the outer wall of the inflatable balloon, and/or 3) the therapeutic material flowing or extruding through the wall of the inflatable balloon. Once treatment by the inflatable balloon is completed, the inflatable balloon is partially or fully deflated and removed from the treatment site. Generally, the deployed stent remains at the treatment site after the inflatable balloon is removed from the treatment site. The ability of the medical device in accordance with the present disclosure to allow the continued flow of blood across the treatment site while the inflatable balloon is inflated and the stent is properly deployed at the treatment site, and the desired amount of any optional therapeutic material is allowed to infuse in desired quantities into the wall of the blood vessel allows for prolonged periods of treatment without asphyxiation of vital organs.

In one non-limiting object of the disclosure is the provision of a medical device and method for treating stenosis by use of an inflatable balloon that enables a therapeutic material to be effectively transferred to the tissue of the blood vessel without preventing the flow of blood through the blood vessel while the inflatable balloon is inflated.

In another non-limiting object of the disclosure is the provision of a medical device and method for treating stenosis by use of an inflatable balloon that optionally promotes diffusion of a therapeutic material into the blood vessel wall without having to puncture the blood vessel wall.

In another non-limiting object of the disclosure is the provision of a medical device and method for treating stenosis by use of an inflatable balloon that provides flexibility to provide the blood vessel wall with therapeutic material, and to optionally continue to provide the blood vessel wall with therapeutic material until a desired saturation point of the therapeutic material within the blood vessel wall is achieved while simultaneously permitting blood flow past the site of treatment.

In another non-limiting object of the disclosure is the provision of a medical device and method for treating stenosis by use of an inflatable balloon that provides the caregiver a flexibility in targeted dose treatment of each patient for a better outcome.

In another non-limiting object of the disclosure is the provision of a medical device and method for treating stenosis by use of a catheter body whose distal end is in communication with an inflatable balloon via an inflation lumen, and wherein the medical device includes a bypass passageway that allows fluid in the blood vessel to move past the inflatable balloon when the inflatable balloon is in a partially or fully inflated state.

In another non-limiting object of the disclosure is the provision of a medical device and method for treating stenosis that includes a bypass passageway that can be formed by 1) a guidewire passageway that is used by the guidewire, and/or 2) a second passageway separate from the guidewire passageway.

In another non-limiting object of the disclosure is the provision of a medical device and method for treating stenosis that includes a bypass passageway that is fully formed by a guidewire passageway, wherein the guidewire passageway is configured to fully pass through the inflatable balloon, and the guidewire passageway includes one or more openings located prior to the location of the inflatable balloon (located prior to the posterior end of the inflatable balloon) and one or more openings located after the location of the inflatable balloon (located after the anterior end of the inflatable balloon).

In another non-limiting object of the disclosure is the provision of a medical device and method for treating stenosis that includes a bypass passageway that is fully formed by a secondary passageway, wherein the secondary passageway is configured to pass fully through the inflatable balloon and the secondary passageway has one or more openings that are located at or prior to the posterior end of the inflatable balloon and also has one or more openings that are located at or after the anterior end of the inflatable balloon.

In another non-limiting object of the disclosure is the provision of a medical device and method for treating stenosis that includes a bypass passageway that is partially formed by the guidewire passageway and partially formed by a secondary passageway, wherein the guidewire passageway is configured to partially or fully pass through the inflatable balloon, and wherein the secondary passageway is configured to partially or fully pass through the inflatable balloon, and wherein the guidewire passageway includes one or more openings located prior to the location of the inflatable balloon (located prior to the posterior end of the inflatable balloon), and wherein the secondary passageway has one or more openings that are located at or after the anterior end of the inflatable balloon.

In another non-limiting object of the disclosure is the provision of a medical device and method for treating stenosis that includes a bypass passageway wherein the one or more openings that are located prior to the anterior or proximal end of the inflatable balloon are located within 0-20 inches (and all values and ranges therebetween) of the anterior or proximal end of the inflatable balloon, and wherein the one or more openings that are located after the posterior or distal end of the inflatable balloon are located within 0-5 (and all values and ranges therebetween) of the posterior or distal end of the inflatable balloon.

In another non-limiting object of the disclosure is the provision of a medical device and method for treating stenosis that includes a bypass passageway wherein the number and size of the one or more openings in the bypass passageway is selected so that at least 5% of the pretreatment fluid flow rate through the blood vessel (e.g., pretreatment fluid flow rate is the flow rate of fluid through the blood vessel prior to the medical device being inserted into the treatment area of the blood vessel) is maintained when the inflatable balloon is 90-100% inflated (and all values and ranges therebetween), and typically at least 10 vol. % of the pretreatment fluid flow rate through the blood vessel is maintained when the inflatable balloon is 90100% inflated in the blood vessel.

In another non-limiting object of the disclosure is the provision of a medical device and method for treating stenosis that includes a single bypass passageway.

In another non-limiting object of the disclosure is the provision of a medical device and method for treating stenosis that includes two or more bypass passageways.

In another non-limiting object of the disclosure is the provision of a medical device and method for treating stenosis wherein when the inflatable balloon is 90%-100% inflated (and all values and ranges therebetween) at the treatment site in the blood vessel, at least 50 vol. % of the fluid that flows through the treatment site and bypasses the inflated inflatable balloon of the medical device flows through the one or more bypass passageways.

In another non-limiting object of the disclosure is the provision of a medical device and method for treating stenosis wherein the medical device optionally includes one or more radiopaque markers to facilitate in positioning the medical device at the treatment site within a blood vessel.

In another non-limiting object of the disclosure is the provision of a medical device and method for treating stenosis wherein the medical device optionally includes one or more radiopaque markers located inside the inflatable balloon.

In another non-limiting object of the disclosure is the provision of a medical device and method treating for stenosis wherein the inflatable balloon of the medical device optionally includes one or more balloon wall openings that are sized to allow the passage of a therapeutic material (e.g., one or more therapeutic agents [e.g., vasodilator, antithrombosis agent, anti-restenosis drug, etc.], one or more coated therapeutic agents (e.g., coated or encapsulated therapeutic agent using an excipient or other type of coating, a solution of one or more therapeutic agents and/or coated therapeutic agents, etc.) to pass through the inflatable balloon wall.

In another non-limiting object of the disclosure is the provision of a medical device and method for treating stenosis wherein the inflatable balloon of the medical device optionally includes one or more balloon wall openings such that the number and size of the one or more balloon wall openings are selected to enable the inflatable balloon to be fully inflated and hold a desired internal pressure in the inflatable balloon.

In another non-limiting object of the disclosure is the provision of a medical device and method for treating stenosis wherein the inflatable balloon of the medical device optionally includes one or more balloon wall openings such that the number and size of the one or more balloon wall openings are selected to enable the inflatable balloon to be fully inflated and hold an internal pressure of 1-20 Atm.

In another non-limiting object of the disclosure is the provision of a medical device and method for treating stenosis wherein the inflatable balloon of the medical device optionally includes one or more balloon wall openings formed by balloon wall pores that have been partially formed in the balloon wall (e.g., pores create a thinner wall thickness in the inflatable balloon wall), but which balloon wall pores do not fully penetrate the balloon wall until after the first inflation of the inflatable balloon, and which balloon wall pores are configured to only form openings through the balloon wall after the inflatable balloon has been inflated, and the stretching of the balloon wall during inflation and/or the internal pressure within the inflatable balloon during inflation causes the balloon wall pores to rupture or open to thereby form balloon wall openings in the balloon wall.

In another non-limiting object of the disclosure is the provision of a medical device and method for treating stenosis wherein the inflatable balloon of the medical device optionally can be foldable into a smaller profile to facilitate in the insertion of the medical device at the treatment area in the blood vessel. The folded inflatable balloon can be configured to unfold and inflate at the treatment site.

In another non-limiting object of the disclosure is the provision of a medical device and method for treating stenosis wherein the medical device is configured optionally to apply therapeutic material to the wall of the blood vessel by 1) causing therapeutic material (e.g., one or more therapeutic agents [e.g., vasodilator, antithrombosis agent, anti-restenosis drug, etc.], one or more coated therapeutic agents (e.g., coated or encapsulated therapeutic agent using an excipient or other type of coating, a solution of one or more therapeutic agents and/or coated therapeutic agents, etc.) to flow or pass through one or more balloon wall openings in the inflated inflatable balloon, 2) coating the outer surface of the inflatable balloon with one or more therapeutic agents, and/or 3) coating the outer surface of the inflatable balloon with one or more coated or encapsulated therapeutic agents.

In another non-limiting object of the disclosure is the provision of a medical device and method for treating stenosis wherein the medical device can optionally include an electrical field-generating element to cause electroporation.

In another non-limiting object of the disclosure is the provision of a medical device and method for treating stenosis wherein the medical device can optionally include an electrical field-generating element that includes one or more electrodes.

In another non-limiting object of the disclosure is the provision of a medical device and method for treating stenosis wherein the medical device can optionally include a side branch passageway that is formed off of the bypass passageway, wherein the side branch passageway can be configured to provide blood at a location between the proximal and distal ends of the inflatable balloon.

In another non-limiting object of the disclosure is the provision of a medical device and method for treating stenosis wherein the medical device can optionally include a second inflatable balloon that is positioned adjacent to the first inflatable balloon or spaced from the first inflatable balloon.

In another non-limiting object of the disclosure is the provision of a medical device and method for treating stenosis wherein the medical device can optionally include a second inflatable balloon positioned adjacent to the first inflatable balloon or spaced from the first inflatable balloon, and wherein the first end of the bypass passageway is configured to include one or more openings at or prior to the proximal end of the first inflatable balloon and the second end of the bypass passageway is configured to include one or more openings at or after the distal end of the second inflatable balloon.

In another non-limiting object of the disclosure is the provision of a medical device and method for treating stenosis wherein the medical device can optionally include a second inflatable balloon positioned adjacent to the first inflatable balloon or spaced from the first inflatable balloon, and optionally includes an auxiliary balloon passageway to fluidly connect the first and second inflatable balloons.

In another non-limiting object of the disclosure is the provision of a medical device and method for treating stenosis wherein the medical device can optionally include a second inflatable balloon positioned adjacent to the first inflatable balloon or spaced from the first inflatable balloon, and wherein the first and/or second inflatable balloons optionally include the one more balloon wall openings to allow therapeutic material to flow or extrude from the first and/or second inflatable balloons onto the blood vessel wall as previously described above with respect to the first inflatable balloon.

In another non-limiting object of the disclosure is the provision of a medical device and method for treating stenosis wherein the medical device can optionally include a second inflatable balloon positioned adjacent to the first inflatable balloon or spaced from the first inflatable balloon, and wherein the first and/or second inflatable balloons optionally include one more electrodes to perform an electroporation treatment.

In another non-limiting object of the disclosure is the provision of a medical device and method for treating stenosis wherein a non-limiting method for using the medical device is as follows: 1) the guide catheter is first introduced into the body and into the vasculature and navigated to the close proximity of the treatment site, 2) a guide wire is then navigated through the guide catheter and extended past the treatment site, 3) the medical device in accordance with the present disclosure is introduced over the guide wire, through the guide catheter, and navigated to the treatment site such that the inflatable balloon of the medical device is placed across the treatment site, and optional markers on the medical device can be used in the proper positioning of the medical device at the treatment site, 4) the inflatable balloon is then pressurized with a fluid, which fluid can optionally include a therapeutic material (e.g., one or more therapeutic agents [e.g., vasodilator, antithrombosis agent, anti-restenosis drug, etc.], one or more coated therapeutic agents (e.g., coated or encapsulated therapeutic agent using an excipient or other type of coating, a solution of one or more therapeutic agents and/or coated therapeutic agents, etc.), 5) as the inflatable balloon in inflated, the inflatable balloon expands and the outer wall of the inflatable balloon apposes against the wall of the blood vessel at the treatment site, and the expansion of the inflatable balloon can optionally increase the cross-sectional area of the opening in the treatment area of the blood vessel, 6) when the inflatable balloon is fully deployed (e.g., fully inflated at the treatment area), blood flow about the inflatable balloon is substantially or fully terminated except for the continued flow of blood about the inflated inflatable balloon via the one or more bypass passageways in the medical device, 7) therapeutic material can optionally be applied to the wall of the blood vessel that is closely adjacent to or in contact with the inflatable balloon at the treatment site by a) flowing therapeutic material into the interior of the inflatable balloon and causing the therapeutic material (e.g., one or more therapeutic agents [e.g., vasodilator, antithrombosis agent, anti-restenosis drug, etc.], one or more coated therapeutic agents (e.g., coated or encapsulated therapeutic agent using an excipient or other type of coating, a solution of one or more therapeutic agents and/or coated therapeutic agents, etc.) to flow or pass through one or more balloon wall openings in the inflated inflatable balloon, b) coating the outer surface of the inflatable balloon with one or more therapeutic agents, and/or c) coating the outer surface of the inflatable balloon with one or more coated or encapsulated therapeutic agents, 8) the inflatable balloon can remain inflated at the treatment site as long as needed for proper treatment of the blood vessel (e.g., allow sufficient time for one or more therapeutic agents to infuse in desired quantities into the wall of the blood vessel, etc.), and 9) once the treatment of the blood vessel is complete, the inflatable balloon can be partially or fully deflated and the inflatable balloon, guide wire, guide wire catheter, etc., can be removed from the blood vessel.

In another non-limiting object of the disclosure is the provision of a medical device and method for treating stenosis wherein a non-limiting method for using the medical device includes the optional additional step, prior to the inflatable balloon, guide wire, guide wire catheter, etc., being removed from the blood vessel, the inflatable balloon can be partially or fully deflated at the treatment site and the fluid containing the therapeutic material can optionally be retrieved from the inflatable balloon fluid and, thereafter, the balloon can be filled with a high viscosity solution having particles that resist or cannot pass through the one or more balloon wall openings so that the inflatable balloon can be inflated to a higher pressure that could be achieved when the inflatable balloon was inflated by a solution that included the therapeutic material.

In another non-limiting object of the disclosure is the provision of a medical device and method for treating stenosis wherein a non-limiting method for using the medical device includes the optional additional step of inflating the inflatable balloon at higher internal pressures to expand the opening at the treatment area to a desired size prior to the removal of the inflatable balloon from the treatment site.

In another non-limiting object of the disclosure is the provision of a medical device and method for treating stenosis wherein a non-limiting method for using the medical device includes optionally not partially or fully withdrawing the therapeutic material from the inflatable balloon prior to inserting a high viscosity solution into the inflatable balloon to inflate the inflatable balloon, wherein the high viscosity solution can optionally be used to 1) partially or fully plug the one or more balloon wall openings to partially or fully prevent further therapeutic material from passing through the balloon wall openings, or 2) partially plug the one or more balloon wall openings to require higher internal pressures to allow the therapeutic material to pass through the balloon wall openings.

In another non-limiting object of the disclosure is the provision of a medical device and method for treating stenosis wherein a non-limiting method for using the medical device includes inflating the inflatable balloon by a fluid that is or includes a radiopaque liquid (e.g., a contrast agent).

In another non-limiting object of the disclosure is the provision of a medical device and method for treating stenosis wherein a non-limiting method for using the medical device includes the steps of 1) the inflatable balloon is inserted at the treatment site, 2) the inflatable balloon is partially of fully inflated with a fluid that is or includes a radiopaque liquid, 3) the position of the inflatable balloon at the treatment site is verified and/or adjusted based on the viewing of the radiopaque liquid in the partially or fully inflated inflatable balloon, 4) the radiopaque liquid is optionally fully or partially withdrawn from the inflatable balloon after the inflatable balloon has been verified to be in the proper position in the treatment site, 5) the inflatable balloon is again inflated if the inflatable balloon was partially or fully deflated when the radiopaque liquid was optionally withdrawn from the inflatable balloon, and 6) therapeutic material is optionally inserted into the interior of the inflated inflatable balloon such that therapeutic material can optionally be applied to the wall of the blood vessel by the therapeutic material flowing or extruding through the wall of the inflatable balloon.

In another non-limiting object of the disclosure is the provision of a medical device and method for treating stenosis wherein a non-limiting method for using the medical device includes the optional step of when greater flow of blood is desired across the site of treatment during the inflation of the inflatable balloon and the guidewire catheter is used to partially for fully form a bypass passageway, the guide wire can optionally be retracted back to a point such that the distal end of the guide wire resides proximal to the most proximal opening in the bypass passageway such that the guide wire is not located between any of the openings in the bypass passageway.

In another non-limiting object of the disclosure is the provision of a medical device and method for treating stenosis wherein the medical device can optionally include a stent.

In another non-limiting object of the disclosure is the provision of a medical device and method for treating stenosis wherein the medical device can optionally include a stent, and wherein during the stent deployment, therapeutic material can optionally be applied to the wall of the blood vessel by 1) the therapeutic material being coated on the stent, 2) the therapeutic material being coated on the outer wall of the inflatable balloon, and/or 3) the therapeutic material flowing or extruding through the wall of the inflatable balloon.

In another non-limiting object of the disclosure is the provision of a medical device and method for treating stenosis wherein the inflatable balloon can optionally be inflated by a fluid that is or includes a radiopaque liquid (e.g., a contrast agent), and a therapeutic material can optionally be included in the radiopaque liquid.

In another non-limiting object of the disclosure is the provision of a medical device and method treating stenosis wherein there is provided a medical angioplasty balloon with pores capable of holding pressure and mounted on a catheter wherein, the catheter has a passageway that connects the proximal end of the balloon to the proximal end of the catheter, such that the catheter is capable of providing a passageway for bodily fluids to transfuse across from one side of an arterial stenosis to the other side of that stenosis.

In another non-limiting object of the disclosure is a medical device and method for treating stenosis wherein there is provided a medical angioplasty balloon with pores capable of holding pressure and mounted on a catheter, wherein the catheter has a passageway that connects the proximal end of the balloon to the proximal end of the catheter such that the catheter is capable of providing a passageway for bodily fluids to transfuse across one side of an arterial stenosis to the other side of that stenosis while the balloon is pressurized.

In another non-limiting object of the disclosure is a medical device and method for treating stenosis wherein there is provided a medical angioplasty balloon with pores capable of holding pressure and mounted on a catheter, wherein the catheter has a passageway that connects the proximal end of the balloon to the proximal end of the catheter such that the catheter is capable of providing a passageway for bodily fluids to transfuse across one side of an arterial stenosis to the other side of that stenosis while the balloon is pressurized and exuding fluid.

In another non-limiting object of the disclosure is a medical device and method for treating stenosis wherein there is provided a medical angioplasty balloon with pores capable of holding pressure and mounted on a catheter, wherein the catheter has a passageway that connects the proximal end of the balloon to the proximal end of the catheter such that the catheter is capable of providing a passageway for bodily fluids to transfuse across one side of an arterial stenosis to the other side of that stenosis while the balloon is pressurized and extruding fluid to its outer surface.

In another non-limiting object of the disclosure is a medical device and method for treating stenosis wherein there is provided a medical angioplasty balloon with pores capable of holding pressure and mounted on a catheter, wherein the catheter has a passageway that connects the proximal end of the balloon to the proximal end of the catheter such that the catheter is capable of providing a passageway for bodily fluids to transfuse from one side of an arterial stenosis to the other side of that stenosis while the balloon is pressurized and extruding fluid containing one or more therapeutic substances.

In another non-limiting object of the disclosure is a medical device and method treating stenosis wherein there is provided a medical angioplasty balloon with pores capable of holding pressure and mounted on a catheter, wherein the catheter has a passageway that connects the proximal end of the balloon to the proximal end of the catheter such that the catheter is capable of providing a passageway for bodily fluids to transfuse across one side of an arterial stenosis to the other side of that stenosis while the balloon is pressurized and extruding fluid containing particles comprising of therapeutic substances.

In another non-limiting object of the disclosure is a medical device and method for treating stenosis wherein there is provided a medical angioplasty balloon with pores capable of holding pressure and mounted on a catheter, wherein the catheter has a passageway that connects the proximal end of the balloon to the proximal end of the catheter such that the catheter is capable of providing a passageway for bodily fluids to transfuse from one side of an arterial stenosis to the other side of that stenosis while the balloon is pressurized and extruding fluid containing particles comprising of encapsulated therapeutic substances that can diffuse through the encapsulant.

In another non-limiting object of the disclosure is the provision of a medical device and method for treating stenosis wherein the balloon wall pore size is 0.5-25 microns (and all values and ranges therebetween).

In another non-limiting object of the disclosure is the provision of a medical device and method for treating stenosis having therapeutic agent encapsulated within a polymer having particle size less than 25 microns.

In another non-limiting object of the disclosure is the provision of a medical device and method for treating stenosis wherein the therapeutic agent encapsulated within one or more polymers are comprised of bioresorbable polymer such as, but not limited to, poly lactic acid and its derivatives, polyanhydrides, tyrosine and its derivatives, polyglycolic acid and its derivatives, and wherein the encapsulant is lipophilic or hydrophilic.

In another non-limiting object of the disclosure is a medical device and method for treating stenosis wherein there is provided a medical angioplasty balloon with therapeutic substance or substances laid on the outer surface and mounted on a catheter that is capable of providing a passageway for bodily fluids to transfuse from one side of an arterial stenosis to the other side of that same arterial stenosis.

In another non-limiting object of the disclosure is the provision of a medical device and method treating stenosis wherein a medical angioplasty balloon with particles encapsulating a therapeutic substance or substances are laid on the outer surface and mounted on a catheter that is capable of providing a passageway for bodily fluids to transfuse from one side of an arterial stenosis to the other side of that same arterial stenosis while the balloon is inflated under pressure.

In another non-limiting object of the disclosure is the provision of a medical device and method for treating stenosis wherein there is provided a medical angioplasty balloon with lipophilic particles encapsulating therapeutic substance or multiple therapeutic substances laid on the outer surface and mounted on a catheter that is capable of providing a passageway for bodily fluids to transfuse across from one side of an arterial stenosis to the other side of that same arterial stenosis while the balloon is inflated under pressure.

In another non-limiting object of the disclosure is the provision of a medical device and method for treating stenosis wherein a medical angioplasty balloon having pores capable of holding pressure is mounted on a catheter capable of being pressurized has a stent mounted over it, the stent being expandable into a scaffold to hold the blood vessel open.

In another non-limiting object of the disclosure is the provision of a medical device and method for treating stenosis wherein a medical angioplasty balloon having pores capable of holding pressure is mounted on a catheter capable of being pressurized and extruding fluid and is capable of deploying a stent.

In another non-limiting object of the disclosure is the provision of a medical device and method for treating stenosis wherein a medical angioplasty balloon having pores capable of holding pressure is mounted on a catheter capable of being pressurized and extruding fluid containing therapeutic substance and is capable of deploying a stent.

In another non-limiting object of the disclosure is the provision of a medical device and method for treating stenosis wherein a medical angioplasty balloon having pores capable of holding pressure is mounted on a catheter capable of being pressurized and extruding fluid containing particles comprised of encapsulated therapeutic substance and is capable of deploying a stent.

In another non-limiting object of the disclosure is the provision of a medical device and method treating stenosis wherein a medical angioplasty balloon with pores capable of holding pressure is mounted on a catheter that is capable of being pressurized and extruding fluid containing particles comprised of encapsulated therapeutic substance that can diffuse through the encapsulant which is lipophilic and is capable of deploying a stent.

In another non-limiting object of the disclosure is a medical device and method for treating stenosis wherein there is provided a rapid exchange catheter have a channel that allows the device to slide over a guide wire, the channel extending from the distal tip to anywhere on the catheter body proximal to the said balloon.

In another non-limiting object of the disclosure is the provision of a medical device and method treating stenosis wherein an over-the-wire catheter having a channel that allows the device to slide over a guide wire, the channel extending from the distal tip to the proximal end of the catheter.

In another non-limiting object of the disclosure is a medical device and method for treating stenosis wherein there is provided a catheter having multiple luer connectors opening to the balloon inflation lumen.

In another non-limiting object of the disclosure is the provision of a medical device and method for treating stenosis wherein a medical angioplasty balloon with pores capable of holding pressure is mounted on a catheter, wherein the catheter has a passageway that connects the proximal end of the balloon to the proximal end of the catheter, such that the catheter is capable of providing a passageway for bodily fluids to transfuse across one side of an arterial stenosis to the other side of that stenosis while the balloon is pressurized and extruding fluid containing one or more therapeutic substances, wherein the catheter has two electrodes located outside each end of the balloon and each electrode is connected to an electrical conductive wire extending to the proximal end of the catheter.

In another non-limiting object of the disclosure is the provision of a medical device and method for treating stenosis wherein the catheter has two electrodes, each electrode connected to an electrically conductive wire, and wherein one wire is connected to the positive terminal of an electrical current and the other to the ground.

In another non-limiting object of the disclosure is the provision of a medical device and method for treating stenosis wherein a medical angioplasty balloon with pores capable of holding pressure is mounted on a catheter, wherein the catheter has a passageway that connects the proximal end of the balloon to the proximal end of the catheter such that the catheter is capable of providing a passageway for bodily fluids to transfuse across one side of an arterial stenosis to the other side of that stenosis while the balloon is pressurized and extruding fluid containing one or more therapeutic substances, wherein the catheter has one electrode located within the balloon and is connected to an electrical conductive wire extending to the proximal end of the catheter.

In another non-limiting object of the disclosure is the provision of a medical device and method for treating stenosis wherein there is provided a medical angioplasty catheter having two balloons at the distal end wherein, the two balloons are in communication with each other through a connecting tube, wherein, the catheter has a passageway that connects the proximal end of the catheter to the distal end of the catheter such that the catheter is capable of providing a passageway for bodily fluids to transfuse across from one side of an arterial stenosis to the other side of that stenosis while the two balloons are pressurized, wherein the two balloons are capable of creating and electrical filed across the treatment area wherein, a therapeutic agent is exuded under pressure through the connecting tube between the balloons.

In another non-limiting object of the disclosure is the provision of a medical device and method for treating stenosis wherein a medical device comprises a catheter, a first inflatable balloon mounted on said catheter, and a bypass passageway that enables continued blood flow in a blood vessel and about said first inflatable balloon when said first inflatable balloon is inflated in the blood vessel.

In another non-limiting object of the disclosure is the provision of a medical device and method for treating stenosis wherein said first inflatable balloon includes one or more balloon wall openings.

In another non-limiting object of the disclosure is the provision of a medical device and method for treating stenosis wherein said one or more balloon wall openings has a size of 0.5-25 microns (and all values and ranges therebetween).

In another non-limiting object of the disclosure is the provision of a medical device and method for treating stenosis the inflatable balloon has a balloon wall opening density of 1-25 balloon wall openings per $cm^2$ (and all values and ranges therebetween).

In another non-limiting object of the disclosure is the provision of a medical device and method for treating stenosis wherein said catheter has a passageway in an interior of said first inflatable balloon, a distal portion of said catheter is connected to a proximal portion of said first inflatable balloon.

In another non-limiting object of the disclosure is the provision of a medical device and method for treating stenosis wherein the medical device further includes an expandable stent mounted on an outer surface of said first inflatable balloon.

In another non-limiting object of the disclosure is the provision of a medical device and method for treating stenosis wherein said bypass passageway is partially or fully formed by a) said catheter, b) a guidewire passageway, and/or c) a passageway separate from said catheter and said guidewire passageway.

In another non-limiting object of the disclosure is the provision of a medical device and method for treating stenosis wherein said bypass passageway has a proximal end that is spaced rearwardly of a proximal end of said first inflatable balloon, said bypass passageway has a distal end that is spaced forwardly of a distal end of said first inflatable balloon.

In another non-limiting object of the disclosure is the provision of a medical device and method for treating stenosis wherein said bypass passageway include one or more proximal openings that are located within 20 in. of a proximal end of said first inflatable balloon, said bypass passageway include one or more distal openings that are located within 5 in. of a distal end of said first inflatable balloon.

In another non-limiting object of the disclosure there is the provision of a medical device and method for treating stenosis wherein the medical device further includes one or more luer connectors on said catheter.

In another non-limiting object of the disclosure is the provision of a medical device and method for treating stenosis wherein the medical device further includes a first electrode, said first electrode electrically connected via a wire to a power source spaced rearwardly of a proximal end of said first inflatable balloon, said first electrode located a) inside said first inflatable balloon, b) on an exterior surface of said first inflatable balloon, c) spaced rearwardly of a proximal end of said first inflatable balloon, or d) spaced forwardly of a distal end of said first inflatable balloon.

In another non-limiting object of the disclosure is the provision of a medical device and method for treating stenosis wherein the medical device further includes a second electrode, said second electrode located a) inside said first inflatable balloon, b) on an exterior surface of said first inflatable balloon, c) spaced rearwardly of a proximal end of said first inflatable balloon, or d) spaced forwardly of a distal end of said first inflatable balloon.

In another non-limiting object of the disclosure is the provision of a medical device and method for treating stenosis wherein the medical device further includes a first radiopaque marker, said first radiopaque marker located a) inside said first inflatable balloon, b) on an exterior surface of said first inflatable balloon, c) spaced rearwardly of a proximal end of said first inflatable balloon, or d) spaced forwardly of a distal end of said first inflatable balloon.

In another non-limiting object of the disclosure is the provision of a medical device and method for treating stenosis wherein the medical device further includes a side branch passageway that is at least partially located in said first inflatable balloon, a first end of said side branch passageway fluidly connected to a) said catheter, b) a guidewire passageway, and/or c) a passageway separate from said catheter and said guidewire passageway, a second end of said side branch passageway extending to a wall of said first inflatable balloon or extending outwardly from said wall of said first inflatable balloon.

In another non-limiting object of the disclosure is the provision of a medical device and method for treating stenosis wherein the medical device further includes a second inflatable balloon located forwardly of a distal end of said first inflatable balloon, said first and second inflatable balloons in fluid communication with one another, a supply a fluid to said second inflatable balloon provided by 1) said catheter which also supplies fluid to said first inflatable balloon, and/or 2) an auxiliary balloon passageway that is fluidly connected between said first and second inflatable balloons.

In another non-limiting object of the disclosure is the provision of a medical device and method for treating stenosis wherein the medical device wherein said auxiliary balloon passageway includes one or more wall openings.

In another non-limiting object of the disclosure is the provision of a medical device and method for treating stenosis wherein the medical device further includes a) an electrode located i) inside said second inflatable balloon, ii) on an exterior surface of said second inflatable balloon, iii) spaced rearwardly of a proximal end of said second inflatable balloon, or iv) spaced forwardly of a distal end of said second inflatable balloon; b) a radiopaque marker located i) inside said second inflatable balloon, ii) on an exterior surface of said second inflatable balloon, iii) spaced rearwardly of a proximal end of said second inflatable balloon, or iv) spaced forwardly of a distal end of said second inflatable balloon; c) a stent mounted on said exterior surface of said second inflatable balloon; d) a coating of therapeutic agent on said exterior surface of said second inflatable balloon; and/or e) one or more balloon wall openings in said second inflatable balloon.

In another non-limiting object of the disclosure of a medical device and method for treating stenosis wherein there is provided a method for treating a blood vessel comprising 1) providing a medical device, said medical device comprising a catheter, a first inflatable balloon mounted on said catheter, and a bypass passageway; 2) inserting said medical device into said blood vessel; positioning said medical device at a treatment site in said blood vessel; and 3) inflating said first inflatable balloon at said treatment site; wherein said bypass passageway is configured to enable continued blood flow in said blood vessel and about said first inflatable balloon when said first inflatable balloon is inflated in said blood vessel.

In another non-limiting object of the disclosure is the provision of a medical device and method for treating stenosis wherein said step of inflating includes inserting pressurized fluid into an interior of said first inflatable balloon, said pressurized fluid includes water, blood, blood plasma, saline solution, therapeutic agent, contrast agent, and/or radiopaque agent.

In another non-limiting object of the disclosure is the provision of a medical device and method for treating stenosis wherein said first inflatable balloon includes one or more balloon wall openings, and further includes the step of inserting therapeutic agent into said first inflatable balloon and causing said therapeutic agent to pass through said one or more balloon wall openings while said first inflatable balloon is inflated at said treatment site.

In another non-limiting object of the disclosure is a medical device and method for treating stenosis wherein the method further includes the step of inserting a high viscosity solution into said first inflatable balloon, the high viscosity solution includes particles having an average particle size of 50%-100+% of an average size of said one or more balloon wall openings (and all values and ranges therebetween) while said first inflatable balloon is inflated.

In another non-limiting object of the disclosure is a medical device and method for treating stenosis wherein the step of inflating includes inflating said first inflatable balloon in said blood vessel that is located in a) a brain for a period of greater than 10 seconds without damaging tissue downstream from said first inflatable balloon, or b) a heart that is causing a myocardial infarction for a period of greater than 10 seconds without damaging tissue downstream from said first inflatable balloon.

In another non-limiting object of the disclosure is the provision of a medical device and method for treating stenosis wherein said step of inflating includes inflating said first inflatable balloon in said blood vessel for a period of over 30 seconds without damaging tissue downstream from said first inflatable balloon.

In another non-limiting object of the disclosure is the provision of a medical device and method for treating stenosis wherein the step of inflating includes inflating said first inflatable balloon in said blood vessel for a period of over 60 seconds without damaging tissue downstream from said first inflatable balloon.

In another non-limiting object of the disclosure is the provision of a medical device and method for treating stenosis the step of inflating includes inflating said first inflatable balloon in said blood vessel for a period of up to 15 minutes without damaging tissue downstream from said first inflatable balloon.

In another non-limiting object of the disclosure is the provision of a medical device and method for treating stenosis wherein said medical device further includes a first electrode, said first electrode electrically connected via a wire to a power source spaced rearwardly of a proximal end of said first inflatable balloon, said first electrode located a) inside said first inflatable balloon, b) on an exterior surface of said first inflatable balloon, c) spaced rearwardly of a proximal end of said first inflatable balloon, or d) spaced forwardly of a distal end of said first inflatable balloon, and further includes the step of energizing said first electrode to cause electroporation and/or iontophoresis in said blood vessel to facilitate in the migration of therapeutic agent into tissue of a wall of said blood vessel.

These and other objects and advantages will become apparent from the discussion of the distinction between the disclosure and the prior art and when considering the preferred embodiment shown in the accompanying drawings.

BRIEF DESCRIPTION OF THE DRAWINGS

Reference may now be made to the drawings, which illustrate various embodiments that the disclosure may take in physical form and in certain parts and arrangements of parts wherein:

FIG. 1 illustrates a side view of a non-limiting exemplary embodiment of the medical device that includes an expandable balloon and a bypass passageway in accordance with the present disclosure.

FIG. 1A is an enlarged view of the anterior or proximal end portion of the bypass passageway.

FIG. 4 illustrates a side view of another non-limiting exemplary embodiment of the medical device that includes an expandable balloon and a bypass passageway in accordance with the present disclosure.

FIGS. 4A-4C illustrate non-limiting configurations of electrodes that can be positioned on the medical device in accordance with the present disclosure.

FIG. 8 illustrates a side view of another non-limiting exemplary embodiment of the medical device that includes an expandable balloon and a bypass passageway in accordance with the present disclosure.

FIG. 8A illustrates a side view of another non-limiting exemplary embodiment of the medical device that includes an expandable balloon and a bypass passageway in accordance with the present disclosure.

FIG. 11 illustrates a distal portion of another non-limiting exemplary embodiment of the medical device that includes an expandable balloon and a bypass passageway in accordance with the present disclosure.

FIGS. 11A-11G illustrate various non-limiting balloon wall openings and balloon wall pores that can be formed in the wall of the inflatable balloon.

DETAILED DESCRIPTION OF NON-LIMITING EMBODIMENTS

Figure 2:
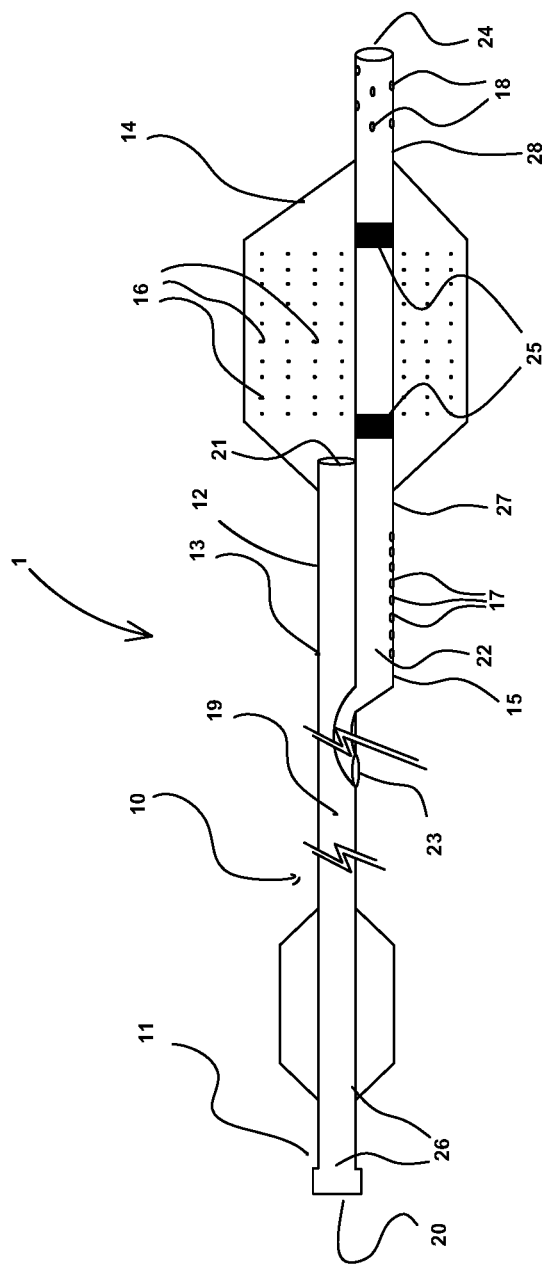
FIG. 2 illustrates a side view of another non-limiting exemplary embodiment of the medical device that includes an expandable balloon and a bypass passageway in accordance with the present disclosure.

A more complete understanding of the articles/devices, processes and components disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of" The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, all the intermediate values and all intermediate ranges).

The terms "about" and "approximately" can be used to include any numerical value that can vary without changing the basic function of that value. When used with a range, "about" and "approximately" also disclose the range defined by the absolute values of the two endpoints, e.g. "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

The present disclosure is directed to a medical device 1 that delivers therapeutic agent to the tissue within the bodily passageway while simultaneously permitting flow of bodily fluids past the location of treatment. The medical device 1 can be configured to deliver a therapeutic material (e.g., therapeutic agent, etc.) to a blood vessel wall where a disease (e.g., vascular stenosis) may have developed. The medical device 1 includes an inflatable balloon 14 that has the capability to inflate and to hold fluid within the inflatable balloon at sufficient pressures (e.g., 1-20 Atm.) to perform a medical procedure without bursting. The inflatable balloon 14 is configured to be used in angioplasty procedures; however, it can be configured for use in other types of procedures.

The medical device 1 can be configured to facilitate in the delivery of a stent 60 in a blood vessel. The medical device 1 can optionally facilitate electroporation and/or iontophoresis for effective delivery of a therapeutic material within the blood vessel wall BV. The inflatable balloon 14 on the medical device 1 is at least partially located at the proximal or distal end of the medical device 1. The wall of the inflatable balloon 14 can optionally include one or more openings or pores 16 that are configured to allow fluid (e.g., a fluid that includes therapeutic material, coloring agent or dye, and/or radiopacity material, etc.) in the interior of the inflatable balloon 14 to flow or extrude through the one or more pores when the inflatable balloon 14 is partially or fully pressurized by the fluid in the interior of the inflatable balloon 14. The fluid that flows or extrudes though the one or more pores in the partially or fully inflated balloon 14 of the medical device 1 and contacts the blood vessel wall BV and can then partially or fully migrates into the tissue of the blood vessel wall BV by diffusion and/or other mechanisms, and which diffusion and/or other mechanisms can optionally be assisted by electroporation and/or iontophoresis.

During the inflation of the inflatable balloon 14 of the medical device 1, the flow of blood through the blood vessel (e.g., vein, artery) is partially or fully maintained across the treatment site by the use of one or more bypass passageways in the medical device 1.

Referring now to FIG. 1, there is illustrated a medical device 1 that includes a catheter body 10. The catheter body 10 includes an elongated body 13 with a passageway 19 extending between the proximal section 11 of the catheter body and distal section 12 of the catheter body. An inflatable balloon 14 is attached to the distal section 12 of the catheter body 10 and the opening 21 in the distal end of passageway 19 is in fluid communication with the inflatable balloon 14.

The passageway 19 of catheter body 10 is illustrated as a tubular section having an opening 20 at the anterior or proximal end of the proximal section 11 of the catheter body 10. Passageway 19 also has an opening 21 at the posterior or distal end of the distal section 12 which is in fluid communication with the inflatable balloon 14. As can be appreciated, the distal section 12 can also or alternatively include one or more wall openings which are in fluid communication with the inflatable balloon 14.

The distal section 12 of the catheter body is illustrated as passing through the anterior or proximal end of the inflatable balloon 14. Generally, the inflatable balloon 14 is secured to and sealed to the distal section 12 of the catheter body 10 by a connection arrangement (e.g., adhesive, melted seam, mechanical connection, etc.). The passageway 19 of the catheter body 10 is used to inflate and deflate the inflatable balloon 14 when the inflatable balloon 14 is located at the treatment site TS in the blood vessel. During the inflation of the inflatable balloon 14, fluid (e.g., therapeutic material, saline solution, blood and/or blood plasma, gas, etc.) is inserted through passageway 19 of catheter body 10 and into the interior of the inflatable balloon 14 to cause inflation of the inflatable balloon 14. Generally, the length of elongated body 13 of the catheter body 10 is such that opening 20 does not enter into the blood vessel during the treatment of the treatment site TS of the blood vessel with the inflatable balloon 14. In one non-limiting arrangement, the length of elongated body 13 of the catheter body 10 is such that opening 20 does not enter the body of a patient during the treatment of the treatment site TS of the blood vessel with the inflatable balloon 14.

The medical device 1 includes guidewire body 15 which is also known as a guide wire lumen. The guidewire body 15 includes a guidewire passageway 22. The guidewire body 15 is configured such that a guidewire (not shown) can pass within guidewire passageway 22. The guidewire is used to guide the medical device to the treatment site TS in the blood vessel.

At least a portion of the guidewire body 15 is positioned generally adjacent elongated body 13 of the catheter body 10. A portion of the guidewire body 15 can be optionally connected to elongated body 13 of the catheter body 10 (e.g., adhesive, melted connection, mechanical connection, etc.). In one non-limiting arrangement, the guidewire body 15 is connected to elongated body 13 of the catheter body 10 at or near the proximal end 27 of the inflatable balloon 14. Guidewire body 15 has a distal end 24 and a proximal end 23. The proximal end 23 of guidewire body 15 is generally located between proximal end 20 and distal end 21 of elongated body 13 of the catheter body 10. Generally, the length of the guidewire body 15 is such that proximal end 23 does not enter into a blood vessel during the treatment of the treatment site TS of the blood vessel with the inflatable balloon 14. In one non-limiting arrangement, the length of the guidewire body 15 is such that proximal end 23 does not enter the body of a patient during the treatment of the treatment site TS of the blood vessel with the inflatable balloon 14.

As illustrated in FIG. 1, the guidewire body 15 extends through the body of the inflatable balloon 14. Generally, the inflatable balloon 14 is secured to and sealed to the guidewire body 15 by a connection arrangement (e.g., adhesive, melted seam, mechanical connection, etc.). As illustrated in FIG. 1, the inflatable balloon 14 is connected to and sealed at the balloon distal end 28 with the guidewire body 15. The proximal end 27 of the inflatable balloon 14 is connected and sealed to both elongated body 13 of the catheter body 10 and guidewire body 15.

The proximal section 11 of the elongated body 13 of the catheter body 10 includes a luer 26 that is communication with opening 20 of the passageway 19 of the catheter body. The luer 26 generally includes threading or some other connection arrangement (not shown) to accommodate a syringe or similar container of fluid reservoir that can be pressurized without leakage. During the inflation of the inflatable balloon 14, fluid is directed into passageway 19 of the catheter body and then into the interior of the inflatable balloon to cause the inflation of the inflatable balloon 14.

The wall of the inflatable balloon 14 can optionally include one or more balloon wall openings 16 that fluidly communicate with the interior of the inflatable balloon 14. The one or more balloon wall openings 16 allow fluid in the interior of the inflatable balloon 14 to flow or extrude out from the interior of the inflatable balloon 14 to the blood vessel wall BV that is located adjacent to or is in contact with the inflatable balloon 14. The size, number, and location of the one or more balloon wall openings 16 on the inflatable balloon 14 are non-limiting. FIGS. 11A-E illustrate a few non-limiting balloon wall opening 16 configurations that can be used. FIGS. 11F-G illustrate balloon wall pores 16' that do not fully penetrate the wall of the inflatable balloon. However, the balloon wall pores 16' are configured to rupture when the inflatable balloon 14 is expanded to form a balloon wall opening 16 such that fluid in the interior of the inflatable balloon 14 can pass fully through the balloon wall opening 16. The balloon wall pores 16' can be formed by removal of certain portions of the inflatable balloon material to create a discontinuity on the surface of the outer and/or inner wall of the inflatable balloon 14. The balloon wall pores 16' can be formed by ablation of the material by a laser or neutron bombardment. The balloon wall openings 16 in the wall of the inflatable balloon 14 can be formed by a hole punch; however, other means can be used.

FIG. 11A illustrates balloon wall opening 16 that has cylindrical shape and has uniform diameter. The diameter of the balloon wall opening 16 can vary from 0.05-10 microns (and all values and ranges therebetween), typically from 1-5 microns, and more typically from 2-4 microns.

FIG. 11B-C illustrate a balloon wall openings 16 that are not of the same shape and/or diameter at the outer surface of the inflatable balloon 14 as at the inner surface of the inflatable balloon 14.

FIG. 11D represents a slit in the wall of the inflatable balloon 14 in which no material has been removed in forming balloon wall opening 16. The perforations can be formed by a single needle punch. The perforations can also be formed by expanding the inflatable balloon 14 in a mold using multiple needles.

The outer surface of the inflatable balloon 14 can optionally be coated with a therapeutic material. When the outer surface of the inflatable balloon 14 is coated with a therapeutic material, the use of the one or more balloon wall openings 16 can be used or eliminated.

Referring again to FIG. 1, the guidewire body 15 includes one or more by proximal bypass openings 17 that are in fluid communication with guidewire passageway 22. The size and number of the one or more proximal bypass openings 17 are non-limiting. The one or more proximal bypass openings 17 is located between the proximal end 23 of the guidewire body and the proximal end 27 of the inflatable balloon 14. As illustrated in FIG. 1, the one or more proximal bypass openings 17 are optionally facing away from the elongated body 13 of the catheter body 10. The one or more proximal bypass openings are located on the guidewire body 15 such that the one or more proximal bypass openings 17 are located in the blood vessel when the inflatable balloon 14 is positioned at the treatment site TS in the blood vessel. Such a location of the one or more proximal bypass openings 17 on the guidewire body 15 allow for blood to flow into the one or more proximal bypass openings 17 and into the guidewire passageway 22 while the inflatable balloon 14 is inflated at the treatment site TS in the blood vessel. In one non-limiting arrangement, the one or more proximal bypass openings 17 are generally located 0-20 in. from the proximal end 27 of the inflatable balloon 14 (and all values and ranges therebetween), typically the one or more proximal bypass openings 17 are located 0-10 in. from the proximal end 27 of the inflatable balloon 14, and more typically the one or more proximal bypass openings 17 are located 0-5 in. from the proximal end 27 of the inflatable balloon 14.

The guidewire body 15 also includes one or more distal bypass openings 18 that are in fluid communication with guidewire passageway 22. A distal bypass opening 18 can also be formed by an opening in the distal end 24 of the guidewire body 15. The size and number of the one or more proximal distal openings 18 are non-limiting. The one or more distal bypass openings 18 is located between the distal end 24 of the guidewire body 15 and the distal end 28 of the inflatable balloon 14. The one or more distal bypass openings 18 are located in the blood vessel when the inflatable balloon 14 is positioned at the treatment site TS in the blood vessel. Such a location of the one or more distal bypass openings 18 on the guidewire body 15 allow for blood that is flowing in the guidewire passageway 22 to exit the guidewire body 15 and into the blood vessel while the inflatable balloon 14 is inflated at the treatment site TS in the blood vessel. In one non-limiting arrangement, the one or more distal bypass openings are generally located 0-5 inches from the distal end 28 of the inflatable balloon 14 (and all values and ranges therebetween), typically the one or more distal bypass openings are located 0-0.5 inches from the distal end 28 of the inflatable balloon 14, and more typically the one or more proximal bypass openings are located 0-0.2 inches from the distal end 27 of the inflatable balloon 14.

The proximal and distal openings 17, 18 have a maximum dimension that is generally smaller than the diameter of the guidewire (not shown) so that the guidewire cannot inadvertently pass through proximal and distal openings 17, 18; however, this is not required. The size of the proximal and distal openings 17, 18 are typically selected such that the guidewire cannot exit through proximal and distal openings 17, 18. For example, in a coronary angioplasty procedure, the typical guidewire has a 0.014 in. in diameter. As such, the maximum dimension of the proximal and distal openings 17, 18 would be less than 0.014 in., and generally no more than 0.013 in. When the medical device 1 is to be used in a peripheral artery procedure, the typical guidewire has a 0.035 in. diameter. As such, the maximum dimension of the proximal and distal openings 17, 18 would be less than 0.035 in., and generally no more than 0.034 in. When the medical device 1 is to be used in a neural application, the typical guidewire has a 0.010 in. diameter. As such, the maximum dimension of the proximal and distal openings 17, 18 would be less than 0.010 in., and generally no more than 0.009 in.

FIG. 1A illustrates non-limiting shapes of the proximal and distal openings 17, 18. The shape of two or more proximal openings 17 can be the same or different. The shape of two or more distal openings 18 can be the same or different. The shape of two or more proximal and distal openings 17, 18 can be the same or different. The orientation and location of the proximal and distal openings 17, 18 on the guidewire body 15 is non-limiting. The spacing of two or more proximal and distal openings 17, 18 is non-limiting. The number of distal openings 18 can be the same or different from the number of proximal openings 17.

The proximal and distal openings 17, 18 illustrated in FIG. 1A have a short axis and long axis to form oval-shaped openings, rectangular openings, etc. As can be appreciated, the shape of the proximal and distal openings 17, 18 can have other shapes (e.g., circular, square, polygonal, etc.).

As illustrated in FIG. 1, proximal openings 17 have a generally circular or oval shape and are located on the side of the guidewire body 15 that is opposite of the elongated body 13 of the catheter body 10 and are spaced apart frp, one another along the longitudinal axis of the guidewire body 15. The shape and size of the proximal openings 17 is generally the same. FIG. 1 illustrates distal openings 18 as having a generally circular or oval shape and are located at various locations about the guidewire body 15. The shape and size of the distal openings 18 is generally the same.

The medical device 1 of FIG. 1 can optionally include one or more radiopaque marker bands 25. The one or more radiopaque marker bands 25 can be attached to the guidewire body 15; however, the one or more radiopaque marker bands 25 can be attached at other locations (e.g., on the inflatable balloon 14, on the distal portion of elongated body 13 of the catheter body 10, etc.). As illustrated in FIG. 1, two radiopaque marker bands 25 are located in the interior of the inflatable balloon 14 wherein one of the radiopaque marker bands 25 is located close to the proximal end 27 of the inflatable balloon 14 and the other radiopaque marker band 25 is located close to the distal end 28 of the inflatable balloon 14. As can be appreciated, one or more of the radiopaque marker bands 25 can be located outside the interior of the inflatable balloon.

The medical device 1 of FIG. 1 can optionally include a stent (not shown) mounted to the outer surface of inflatable balloon 14. During inflation of the inflatable balloon 16, the stent can be caused to expand at the treatment site in the blood vessel. The stent can be optionally coated with a therapeutic agent.

The medical device 1 of FIG. 1 can optionally include a therapeutic agent coating (not shown) coated on the outer surface of inflatable balloon 14.

Referring now to FIG. 2, another non-limiting medical device 1 is illustrated. The medical device is similar to the medical device previously discussed with respect to FIG. 1. However, the proximal end 23 of the guidewire body 15 is connected to the interior of the elongated body 13 of the catheter body 10. The location along the elongated body 13 of the catheter body 10 to which the proximal end 23 of the guidewire body 15 is connected is non-limiting. In operation, the guidewire (not shown) is fed into the passageway 19 of the elongated body 13 of the catheter body 10 via opening 20. Once the guidewire reaches the location along the elongated body 13 of the catheter body 10 to which the proximal end 23 of the guidewire body 15 is connected, the guidewire is further fed into the guidewire passageway 22 of guidewire body 15. The cross-sectional area of a portion or all of the proximal portion of the guidewire passageway 22 of guidewire body 15 that is located prior to the location of proximal openings 17 can optionally be less than a cross-sectional area of a remainder of the guidewire passageway 22 of guidewire body 15.

The medical device 1 of FIG. 2 can optionally include a stent (not shown) mounted to the outer surface of inflatable balloon 14. During inflation of the inflatable balloon 14, the stent can be caused to expand at the treatment site in the blood vessel. The stent can be optionally coated with a therapeutic agent.

The medical device 1 of FIG. 2 can optionally include a therapeutic agent coating (not shown) coated on the outer surface of inflatable balloon 14.

Figure 3:
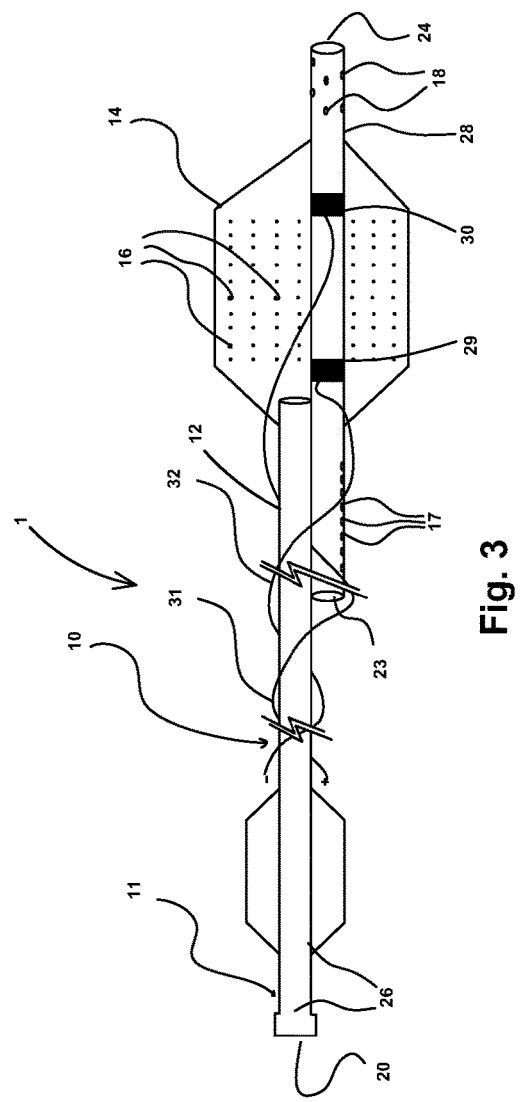
FIG. 3 illustrates a side view of another non-limiting exemplary embodiment of the medical device that includes an expandable balloon and a bypass passageway in accordance with the present disclosure.

Referring now to FIGS. 3, 3A, 3B, and 3C, additional non-limiting medical devices 1 are illustrated. The medical devices 1 are similar to the medical device previously discussed with respect to FIG. 1. However, the guidewire body 15 does not include radiopaque marker band 25, but instead includes two electrically conductive elements or electrodes 29 and 30. The electrodes 29 and 30 are illustrated as attached to the guidewire body 15; however, the one or more electrodes 29 and 30 can be attached at other locations (e.g., on the inflatable balloon 14, on the distal portion of elongated body 13 of the catheter body 10, etc.). As illustrated in FIG. 3, electrodes 29 and 30 are located in the interior of the inflatable balloon wherein electrode 29 is located close to the proximal end 27 of the inflatable balloon 14 and electrode 30 is located close to the distal end 28 of the inflatable balloon 14. Generally, electrodes 29 and 30 are spaced from one another. Electrodes 29 and 30 are connected to wires 32 and 31, respectively. Wires 31 and 32 are typically insulated from each other. As illustrated in FIG. 3, wires 31 and 32 are positioned about elongated body 13 of the catheter body 10 and the ends are connected to a power source (not shown). The electrodes 29 and 30 can be formed of materials that resist corrosion and which are highly conductive. Such materials include, but are not limited to, copper graphite, brass, titanium, silver, platinum, molybdenum, rhenium, tungsten, and their alloys thereof. Electrodes 29 and 30 can be used to facilitate electroporation and/or iontophoresis for effective delivery of a therapeutic material within the wall of the blood vessel.

Figure 15A:
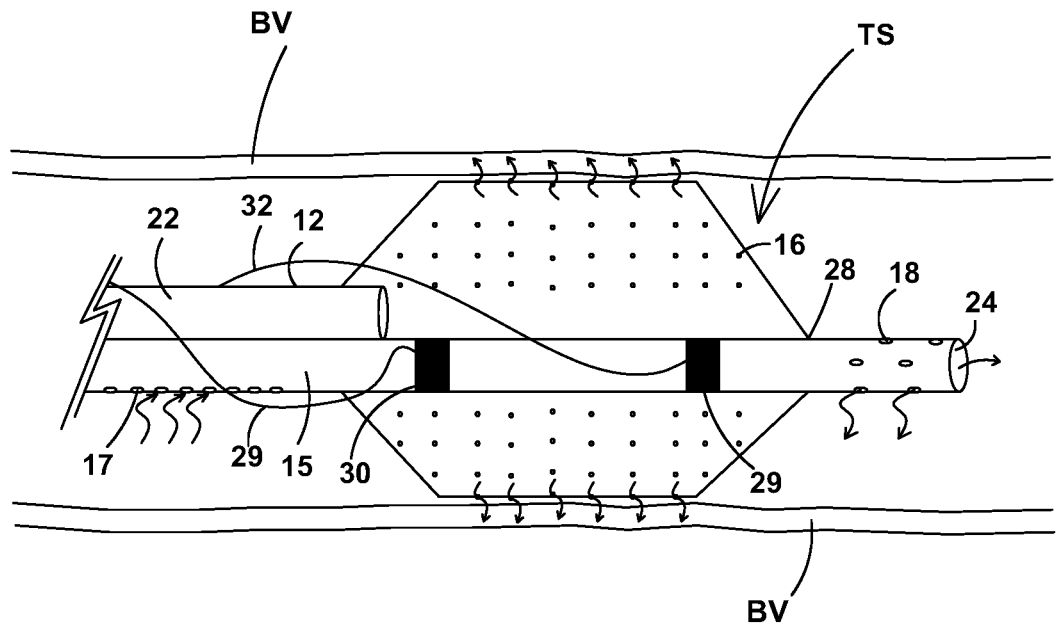
FIG. 15A illustrates an enlarged portion of a blood vessel that includes a non-limiting exemplary embodiment of the medical device that includes an expandable balloon and a bypass passageway in accordance with the present disclosure.

FIG. 15A illustrates an enlarged portion of the medical device 1 of FIG. 3 wherein the inflatable balloon 14 is inflated at the treatment site TS such that the outer surface of the inflatable balloon 14 is located at or closely adjacent to the inner surface of the blood vessel wall BV. While the inflatable balloon is in the inflated state, blood flow through the blood vessel and passed the inflated inflatable balloon continues by the bypass passageway formed by the guidewire body 15. As illustrated in FIG. 15A, blood flows (as illustrated by the arrows) into proximal bypass openings 17 that are in fluid communication with guidewire passageway 22 and which are located at or near the proximal end of inflatable balloon 14. The blood flows into the guidewire passageway 22 via proximal bypass openings 17 and continues flowing in the guidewire passageway 22 until exiting the guidewire body 15 via distal openings 18 in the guidewire body 15 (illustrated by the arrows). As also illustrated in FIG. 15A, fluid that is used to inflate the inflatable balloon 14 can flow out of the inflatable balloon 14 via balloon wall openings 16 (illustrated by the arrows). The fluid exiting the inflatable balloon 14 can include therapeutic agent which can pass into the tissue of the blood vessel wall BV.

Figure 15B:
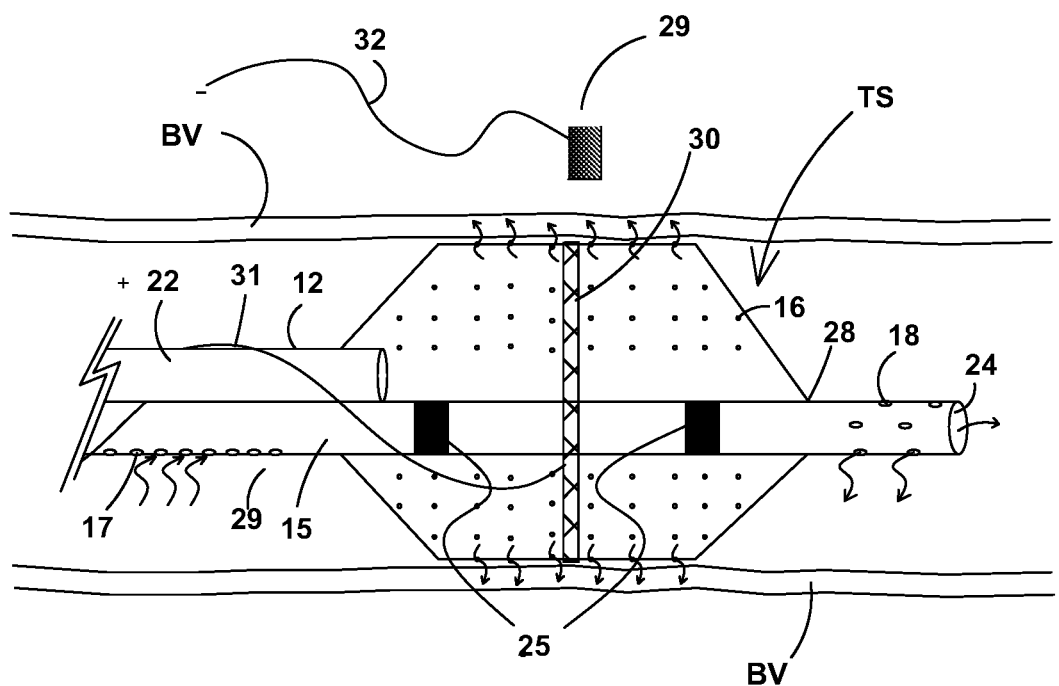
FIG. 15B illustrates enlarged portion of a blood vessel that includes a non-limiting exemplary embodiment of the medical device that includes an expandable balloon and a bypass passageway in accordance with the present disclosure.

Referring now to FIG. 15B, there is another enlarged portion of the medical device 1. The medical device 1 illustrated in FIG. 15B is similar to the medical device illustrated in FIG. 15A except that the medical device 1 illustrated in FIG. 15B includes two radiopaque markers 25 on the guidewire body 15 instead of electrodes 29, 30 as illustrated in FIG. 15A. Also, the medical device 1 illustrated in FIG. 15B includes an electrode 30 positioned on the outer surface of inflatable balloon 14. Electrode 30 is connected by wire 31 to a power source (not shown). An electrode 29 can optionally be placed on or above the surface of the patient's body and in close proximity to electrode 30 (e.g., no more than 6 in., no more than 3 in., etc.). The use of second electrode 29 is optional when the electrode 30 is an anode capable of imparting the therapeutic charge in the blood vessel.

Similar in operation of the medical device 1 illustrated in FIG. 15A, the medical device 1 illustrated in FIG. 15B has an inflatable balloon 14 that is inflated at the treatment site TS such that the outer surface of the inflatable balloon 14 is located at or closely adjacent to the inner surface of the blood vessel wall BV. While the inflatable balloon is in the inflated state, blood flow through the blood vessel and passed the inflated inflatable balloon continues by the bypass passageway formed by the guidewire body 15. As illustrated in FIG. 15B, blood flows (as illustrated by the arrows) into proximal bypass openings 17 that are in fluid communication with guidewire passageway 22 and which are located at or near the proximal end of inflatable balloon 14. The blood flows into the guidewire passageway 22 via proximal bypass openings 17 and continues flowing in the guidewire passageway 22 until exiting the guidewire body 15 via distal openings 18 in the guidewire body 15 (illustrated by the arrows). As also illustrated in FIG. 15B, fluid that is used to inflate the inflatable balloon 14 can flow out of the inflatable balloon via balloon wall openings 16 (illustrated by the arrows). The fluid exiting the inflatable balloon 14 can include therapeutic agent which can pass into the tissue of the blood vessel wall BV. Electrodes 29 and 30 facilitate therapeutic material absorption and/or migration into the blood vessel wall using electroporation and/or iontophoresis.

Figure 3A:
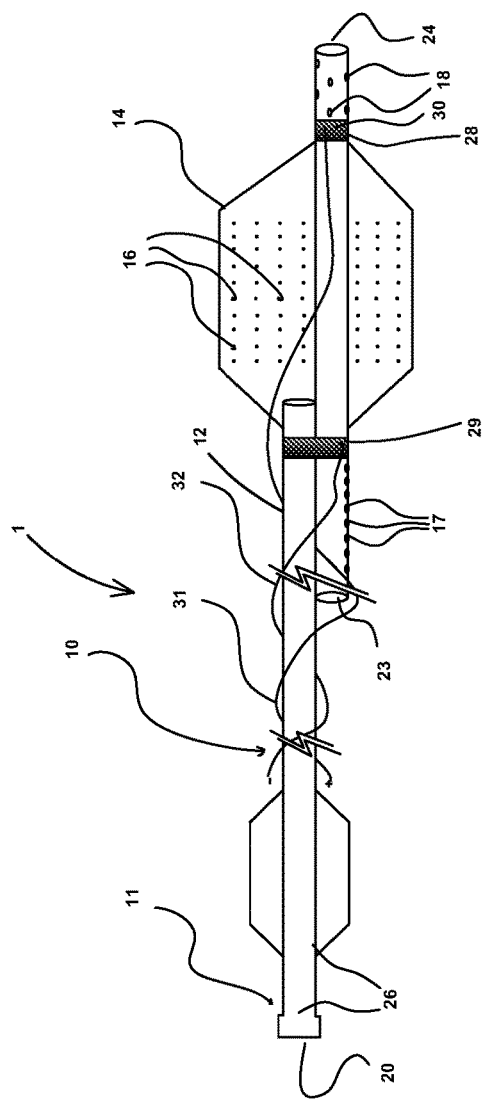
FIG. 3A illustrates a side view of another non-limiting exemplary embodiment of the medical device that includes an expandable balloon and a bypass passageway in accordance with the present disclosure.
Figure 3B:
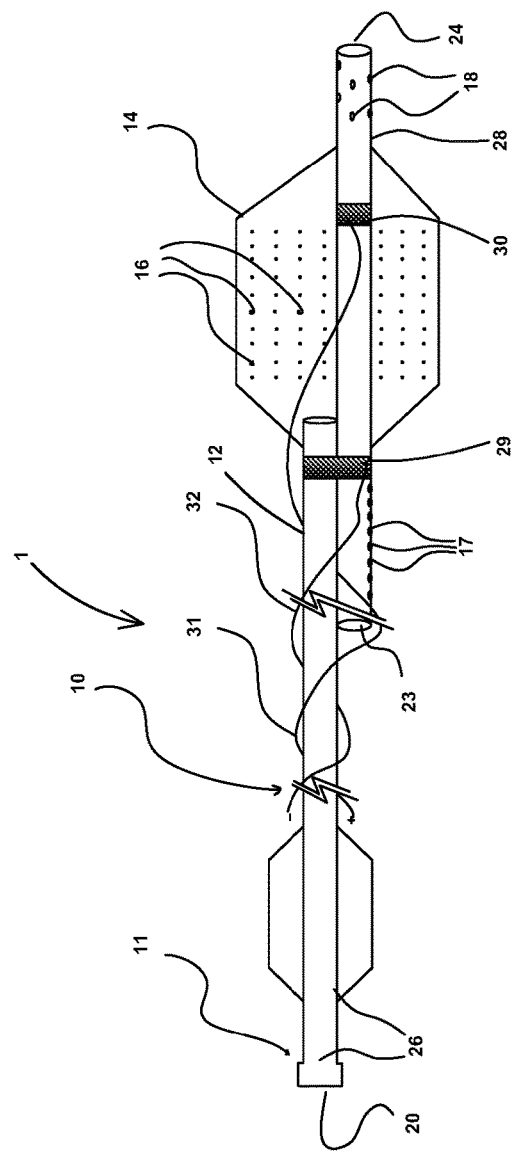
FIG. 3B illustrates a side view of another non-limiting exemplary embodiment of the medical device that includes an expandable balloon and a bypass passageway in accordance with the present disclosure.
Figure 3C:
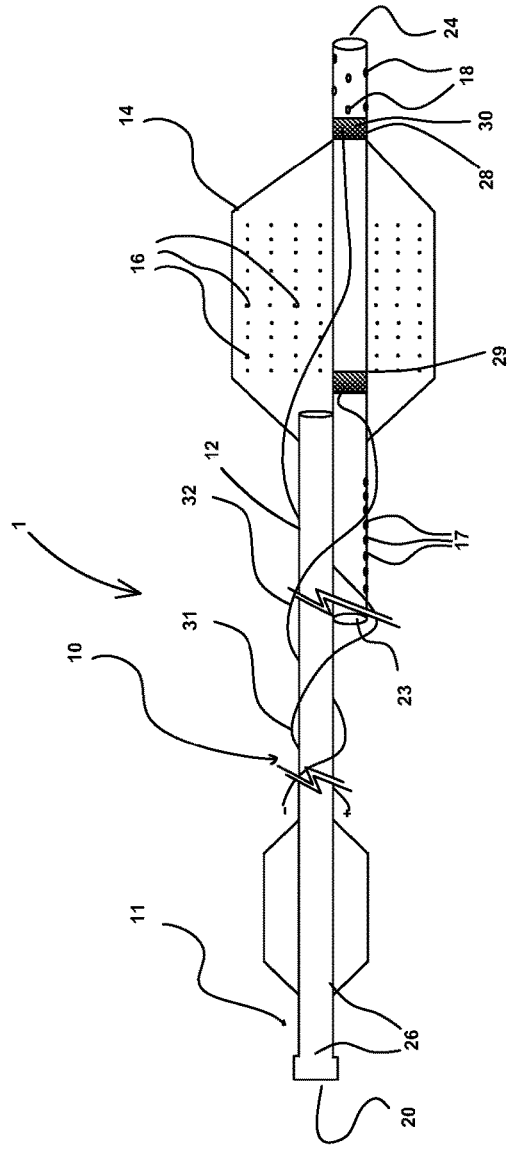
FIG. 3C illustrates a side view of another non-limiting exemplary embodiment of the medical device that includes an expandable balloon and a bypass passageway in accordance with the present disclosure.

FIGS. 3A-C illustrate a medical device 1 having the same configuration as illustrated in FIG. 3 except for the locations of electrodes 29 and 30 on the medical device 1.

FIG. 3A illustrates that electrodes 29 and 30 are both located outside the proximal and distal ends of the inflatable balloon 14, respectively. Electrode 29 is illustrated as being positioned about the both the elongated body 13 of the catheter body 10 and guidewire body 15, and electrode 30 is located about guidewire body 15.

FIG. 3B illustrates that electrode 29 is located outside inflatable balloon 14 near the proximal end 27 of the inflatable balloon 14. Electrode 29 is illustrated as being positioned about both the elongated body 13 of the catheter body 10 and guidewire body 15. Electrode 30 is located within the inflatable balloon 14 and is located about guidewire body 15 near the distal end 28 of the inflatable balloon 14.

FIG. 3C illustrates that electrode 29 is located inside inflatable balloon 14 near the proximal end 27 of the inflatable balloon 14. Electrode 29 is illustrated as being positioned about guidewire body 15. Electrode 30 is located outside the inflatable balloon 14 and is located about guidewire body 15 near the distal end 28 of the inflatable balloon 14.

The medical device 1 of FIGS. 3-3C can optionally include a stent (not shown) mounted to the outer surface of inflatable balloon 14. During inflation of the inflatable balloon 16, the stent can be caused to expand at the treatment site in the blood vessel. The stent can be optionally coated with a therapeutic agent.

The medical device 1 of FIGS. 3-3C can optionally include a therapeutic agent coating (not shown) coated on the outer surface of inflatable balloon 14.

The medical device 1 of FIGS. 3-3C can optionally include one or more radiopaque marker bands (not shown).

Referring now to FIG. 4, another non-limiting medical device 1 is illustrated. The medical device is similar to the medical device previously discussed with respect to FIG. 3. However, the medical device 1 only includes a single electrode 30. Electrode 30 is located inside the inflatable balloon 14. The length of electrode 30 is illustrated as being greater than the length of electrode 30 in FIGS. 3-3C; however, this is not required. In one non-limiting embodiment, the longitudinal length of electrode 30 is at least 25% a longitudinal length of the inflatable balloon 14, typically the longitudinal length of electrode 30 is at least 50% a longitudinal length of the inflatable balloon 14 and, more typically the longitudinal length of electrode 30 is at least 60% a longitudinal length of the inflatable balloon 14.

When the inflatable balloon 14 is positioned at the treatment site TS in the blood vessel, a second electrode 33 can optionally be placed on or above the surface of the patient's body and in close proximity to electrode 30 (e.g., no more than 6 in., no more than 3 in., etc.). The use of second electrode 33 is optional when the electrode 30 is an anode capable of imparting the therapeutic charge in the blood vessel. Electrode 30 can be formed of materials that resist corrosion and which are highly conductive. Such materials include, but are not limited to, copper graphite, brass, titanium, silver, platinum, molybdenum, rhenium, tungsten, and their alloys thereof.

FIGS. 4a-4c illustrate various non-limiting shapes and configurations of electrode 30. FIG. 4a illustrates electrode 30 having a circular band front portion with a plurality of arms extending from the circular band. FIG. 4b illustrates a helical-shaped electrode 30. FIG. 4c illustrates electrode 30 as a solid or meshed-formed tubular band.

The medical device 1 of FIG. 4 can optionally include a stent (not shown) mounted to the outer surface of inflatable balloon 14. During inflation of the inflatable balloon 16, the stent can be caused to expand at the treatment site in the blood vessel. The stent can be optionally coated with a therapeutic agent.

The medical device 1 of FIG. 4 can optionally include a therapeutic agent coating (not shown) coated on the outer surface of inflatable balloon 14.

The medical device 1 of FIG. 4 can optionally include one or more radiopaque marker bands (not shown).

Figure 5:
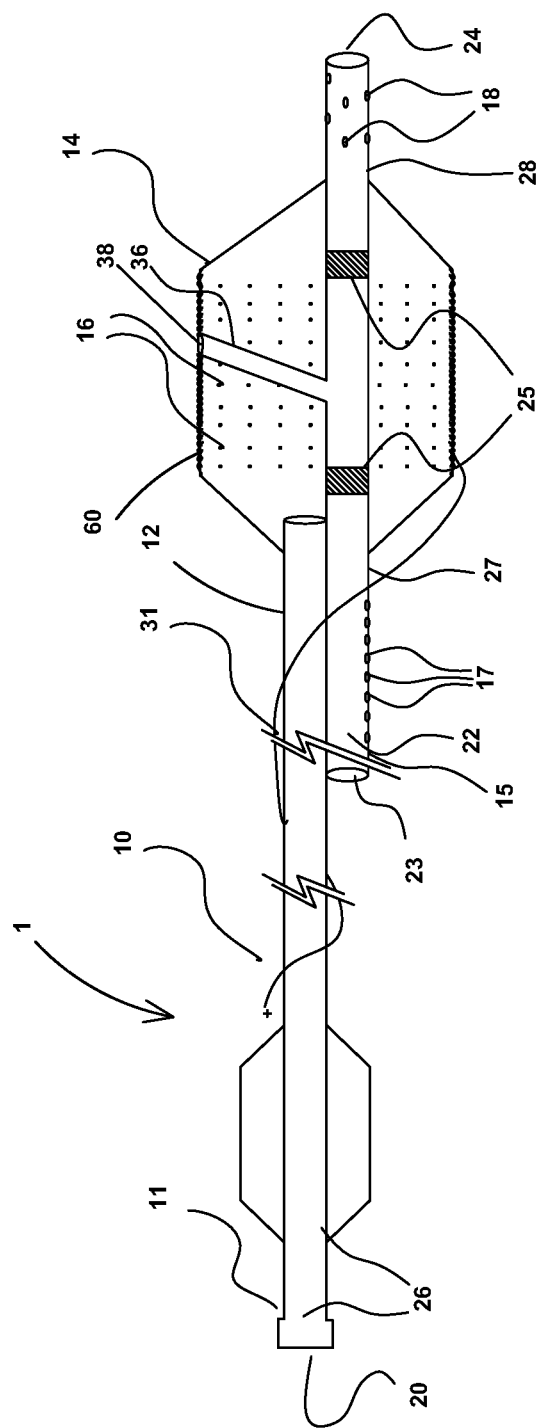
FIG. 5 illustrates a side view of another non-limiting exemplary embodiment of the medical device that includes an expandable balloon and a bypass passageway in accordance with the present disclosure.

Referring now to FIG. 5, another non-limiting medical device 1 is illustrated. The medical device is similar to the medical device previously discussed with respect to FIG. 1. However, a first end of a side branch passageway 36 is fluidly connected to the guidewire body 15 inside the inflatable balloon 14, and a second end of the side branch passageway 36 includes a branch opening 38 that is formed on or extends outwardly from the inflatable balloon 14. Branch opening 38 can be located anywhere between the proximal end 39 and distal end 40 of the inflatable balloon 14. The side branch passageway 36 can be used to supply blood flow to blood vessel wall BW at the location of the treatment site TS when the inflatable balloon 14 has been inflated. The side branch passageway 36 can optionally be formed partially or fully of a flexible material (e.g., flexible polymer, etc.) to facilitate in the optionally movement of the side branch passageway 36 during the inflation and/or deflation of the inflatable balloon 14. As can be appreciated, more than one side branch passageway 36 can be located inside inflatable balloon 14.

A stent 60 can optionally be mounted to the outer surface of the inflatable balloon 14. The stent can optionally include a therapeutic agent coating. When a stent 60 is used, a wire 31 can optionally be releasably positioned in and/or on one or more struts of the stent such that the stent 60 can function as an electrode to facilitate electroporation and/or iontophoresis. When the stent 60 is expanded, wire 31 (when used) can remain in contact with the stent 60. Once the inflatable balloon 14 is removed from the treatment site, wire 31 can also be disconnected from the stent 60 while the expanded stent 60 remains at the treatment site TS in the blood vessel. As can be appreciated, the stent 60 can be substituted for an electrode that is mounted on the outside of the inflatable balloon 14.

As can be appreciated, reference number 60 can alternatively represent a therapeutic agent coating on the outer surface of the outer surface of the inflatable balloon 14 instead of a stent. In such an arrangement, wire 31 is not used.

The medical device 1 of FIG. 4 can optionally include one or more electrodes (not shown) that are located inside the inflatable balloon and/or are located at a location that is distal or proximal to the inflatable balloon 14.

Figure 6:
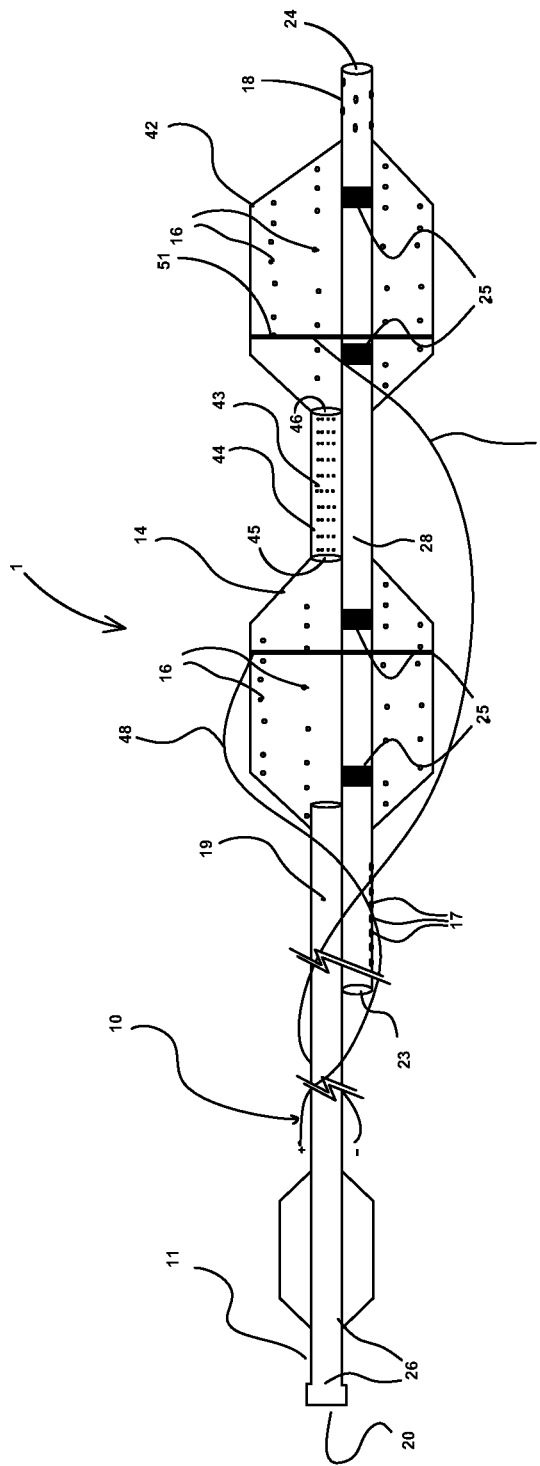
FIG. 6 illustrates a side view of another non-limiting exemplary embodiment of the medical device that includes two expandable balloons and a bypass passageway in accordance with the present disclosure.

Referring now to FIG. 6, another non-limiting medical device 1 is illustrated. The medical device is similar to the medical device previously discussed with respect to FIG. 1. However, the medical device 1 includes a second inflatable balloon 42 that is connected to the guidewire body 15 at a location that is distal to the distal end 28 of inflatable balloon 14, and the inflatable balloons 14 and/or 42 can optionally include balloon wall openings 16.

Inflatable balloons 14 and 42 are illustrated as being spaced from one another; however, this is not required. The size, shape, and configuration of inflatable balloons 14 and 42 can be the same or different. As illustrated in FIG. 6, the size, shape, and configuration of inflatable balloons 14 and 42 is the same.

An auxiliary balloon passageway 43 that is optionally in the form of a tube is used to fluidly connect together the inflatable balloons 14 and 42. As such, when fluid is supplied to inflatable balloon 14 to cause inflation of inflatable balloon 14, fluid that flows into the interior of inflatable balloon 14 can flow into and through auxiliary balloon passageway 43 and into the interior of inflatable balloon 42 to cause inflation of inflatable balloon 42. The auxiliary balloon passageway 43 can optionally include one or more openings 44 that allow fluid flowing though the auxiliary balloon passageway to also flow into the region between to the two inflatable balloons 14, 42. The number, size, and shape of the one or more openings 44 is non-limiting. The auxiliary balloon passageway 43 can be connected and sealed to the inflatable balloons 14 and 42 by a connection arrangement (e.g., adhesive, melted connection, mechanical connection, etc.). The proximal end of the auxiliary balloon passageway 43 is fluidly connected to the interior of inflatable balloon 14 via opening 45. The distal end of the auxiliary balloon passageway 43 is fluidly connected to the interior of inflatable balloon 42 via opening 46. Auxiliary balloon passageway 43 can optionally be connected to guidewire body 15 by a connection arrangement (e.g., adhesive, melted connection, mechanical connection, etc.).

As can be appreciated, auxiliary balloon passageway 43 can be eliminated and catheter body 13 can extend fully through inflatable balloon 14 and partially into inflatable balloon 42. In such an alternative arrangement, catheter body 13 would include one or more wall openings in the interior of inflatable balloon 14 so that fluid can flow out of catheter body 13 and into the interior of inflatable balloon 14 to inflate the inflatable balloon. The opening 21 at the distal end of the catheter body 13 can be used to inflate the interior of inflatable balloon 42 with fluid.

Inflatable balloon 14 and/or inflatable balloon 42 can optionally include one or more balloon wall openings to allow fluid and/or therapeutic material in the interior of the inflatable balloons to flow through the one or more balloon wall openings and to the wall of the blood vessel at the treatment site.

As illustrated in FIG. 6, guidewire body 15 extends through both inflatable balloon 14 and inflatable balloon 42 and the distal portion of the guidewire body 15 extends outwardly from the distal end of inflatable balloon 42. The guidewire body 15 includes one or more proximal bypass openings 17 that are in fluid communication with guidewire passageway 22 and which are located at or near the proximal end of inflatable balloon 14. The guidewire body 15 also includes one or more distal proximal bypass openings 18 and/or opening 24 that are in fluid communication with guidewire passageway 22 and which are located at or near the distal end of inflatable balloon 42. The proximal bypass openings in combination to the distal proximal bypass openings 18 and/or opening 24 allow for continued blood flow past inflatable balloons 14, 42 when one or more of inflatable balloons 14, 42 are inflated.

Medical device 1 optionally includes one or more radiopaque marker bands 25 in inflatable balloon 14 and/or one or more radiopaque marker bands 52 in inflatable balloon 42. As can be appreciated, when one or more radiopaque marker bands are used, the location of one or more radiopaque marker bands can be in locations other than the interior of inflatable balloons 14, 42.

Medical device 1 optionally includes an electrode 50 attached to the outer surface of inflatable balloon 14 and electrode 51 attached to the outer surface of inflatable balloon 42. One end of the wire 48 is attached to electrode 50 and extends to the proximal end of the catheter body 13. Another wire 49 is connected to electrode 51 and also extends to the proximal end of the catheter body. Wires 48 and 49 are generally electrically insulated and/or spaced from one another to not create a short circuit when the wires are energized.

The medical device 1 of FIG. 6 can optionally include a stent (not shown) mounted to the outer surface of inflatable balloon 14. During inflation of the inflatable balloon 16, the stent can be caused to expand at the treatment site in the blood vessel. The stent can be optionally coated with a therapeutic agent.

The medical device 1 of FIG. 6 can optionally include a therapeutic agent coating (not shown) coated on the outer surface of inflatable balloon 14.

The medical device 1 of FIG. 6 can optionally include one or more electrodes (not shown) that are located inside the inflatable balloon and/or are located at a location that is distal or proximal to the inflatable balloon 14.

Figure 7:
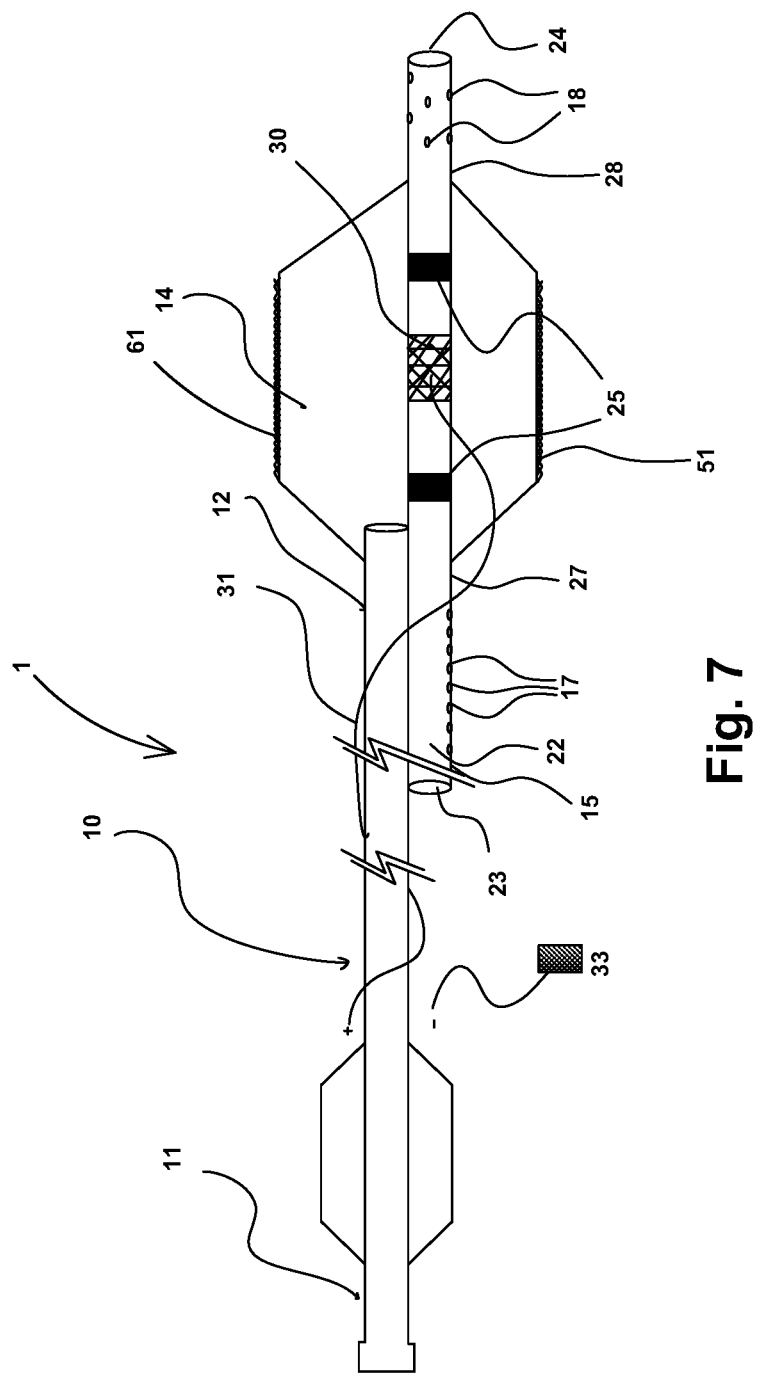
FIG. 7 illustrates a side view of another non-limiting exemplary embodiment of the medical device that includes an expandable balloon and a bypass passageway in accordance with the present disclosure.

Referring now to FIG. 7, another non-limiting medical device 1 is illustrated. The medical device is similar to the medical device previously discussed with respect to FIG. 1. However, the medical device 1 includes an inflatable balloon 14 that is coated with a therapeutic material 61. Although not illustrated in FIG. 7, inflatable balloon 14 can optionally include one or more balloon wall openings to allow fluid and/or therapeutic material in the interior of the inflatable balloons to flow through the one or more balloon wall openings and to the wall of the blood vessel at the treatment site.

An electrode 30 is optionally located in the interior of inflatable balloon 14. Wire 31 is connected to electrode 30. Wire 31 is connected to guidewire body 15 that extends to the proximal section 11 of catheter body 10. When the inflatable balloon 14 is positioned at the treatment site TS in the blood vessel, a second electrode 33 can optionally be placed be placed on or above the surface of the patient's body and in close proximity to electrode 30 (e.g., no more than 6 inches, no more than 3 in., etc.).

The use of second electrode 33 is optional when the electrode 30 is an anode capable of imparting the therapeutic charge in the blood vessel.

A stent 60 can be optionally be mounted over inflatable balloon 14. When a stent 60 is used, electrode 30 can be eliminated and wire 31 can be releasably positioned in the struts of the stent (not shown) such that the stent 60 performs the same function as electrode 30. When the stent is expanded, wire 31 can remain in contact with the stent 60. Once the inflatable balloon 14 is removed from the treatment site, the wire 31 can also be disconnected from the stent 60 while the expanded stent 60 remains at the treatment site in the blood vessel. As can be appreciated, the stent 60 can be substituted for an electrode that is mounted on the outside of the inflatable balloon. As also can be appreciated, reference number 60 can represent a therapeutic agent coating on the outer surface of the outer surface of the inflatable balloon 14 instead of a stent. In such an arrangement, wire 31 is not used.

Referring now to FIG. 8, another non-limiting medical device 1 are illustrated. The medical device is similar to the medical device previously discussed with respect to FIG. 1. However, the guide wire passageway 22 between opening 23 and 24 runs from the extreme distal end of the medical device to the extreme proximal end of the medical device.

The medical device 1 of FIG. 8 can optionally include a stent (not shown) mounted to the outer surface of inflatable balloon 14. During inflation of the inflatable balloon 16, the stent can be caused to expand at the treatment site in the blood vessel. The stent can be optionally coated with a therapeutic agent.

The medical device 1 of FIG. 8 can optionally include a therapeutic agent coating (not shown) coated on the outer surface of inflatable balloon 14.

The medical device 1 of FIG. 8 can optionally include one or more electrodes (not shown) that are located inside the inflatable balloon, at a location that is distal or proximal to the inflatable balloon 14, and/or on an outer surface of the inflatable balloon 14.

Referring now to FIG. 8A, another non-limiting medical device 1 are illustrated. The medical device is similar to the medical device previously discussed with respect to FIG. 3. However, the guide wire passageway 22 between opening 23 and 24 runs from the extreme distal end of the medical device to the extreme proximal end of the medical device.

The medical device 1 of FIG. 8 can optionally include a stent (not shown) mounted to the outer surface of inflatable balloon 14. During inflation of the inflatable balloon 16, the stent can be caused to expand at the treatment site in the blood vessel. The stent can be optionally coated with a therapeutic agent.

The medical device 1 of FIG. 8 can optionally include a therapeutic agent coating (not shown) coated on the outer surface of inflatable balloon 14.

The medical device 1 of FIG. 8 can optionally include one or more electrodes (not shown) that are located inside the inflatable balloon, located at a location that is distal or proximal to the inflatable balloon 14, and/or on an outer surface of the inflatable balloon 14.

Figure 9:
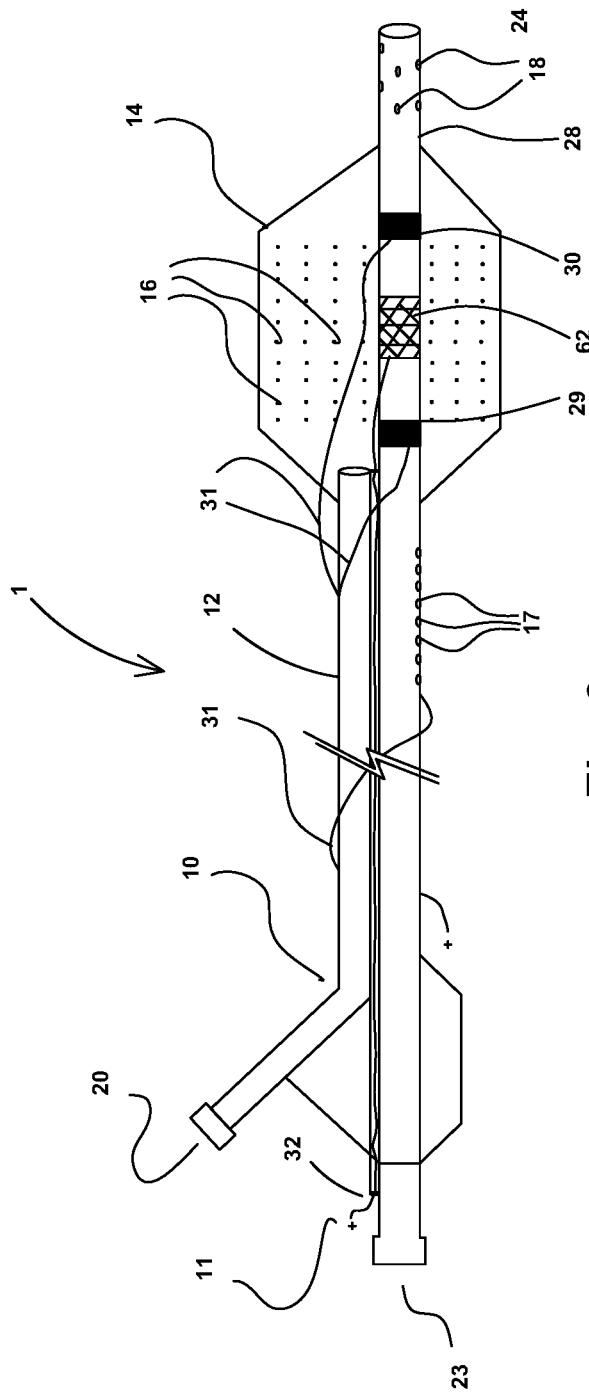
FIG. 9 illustrates a side view of another non-limiting exemplary embodiment of the medical device that includes an expandable balloon and a bypass passageway in accordance with the present disclosure.

Referring now to FIG. 9, another non-limiting medical device 1 is illustrated. The medical device is similar to the medical device previously discussed with respect to FIG. 1. However, the medical device 1 includes three electrodes 29, 30 and 62 located in the interior of inflatable balloon 14. The middle electrode 62 has one type of charge while electrodes 29 and 30 have a charge that is opposite electrode 62. Wire 31 is connected to electrodes 29 and 30 and wire 32 is connected to electrode 62. Although the three electrodes are illustrated as all being located in the interior of inflatable balloon 14, it will be appreciated that one or more electrodes can be located on the outer wall of the inflatable balloon 14 and/or external to the inflatable balloon 14.

The medical device 1 of FIG. 9 can optionally include a stent (not shown) mounted to the outer surface of inflatable balloon 14. During inflation of the inflatable balloon 16, the stent can be caused to expand at the treatment site in the blood vessel. The stent can be optionally coated with a therapeutic agent.

The medical device 1 of FIG. 9 can optionally include a therapeutic agent coating (not shown) coated on the outer surface of inflatable balloon 14.

The medical device 1 of FIG. 9 can optionally include one or more radiopaque marker bands (not shown).

Figure 10:
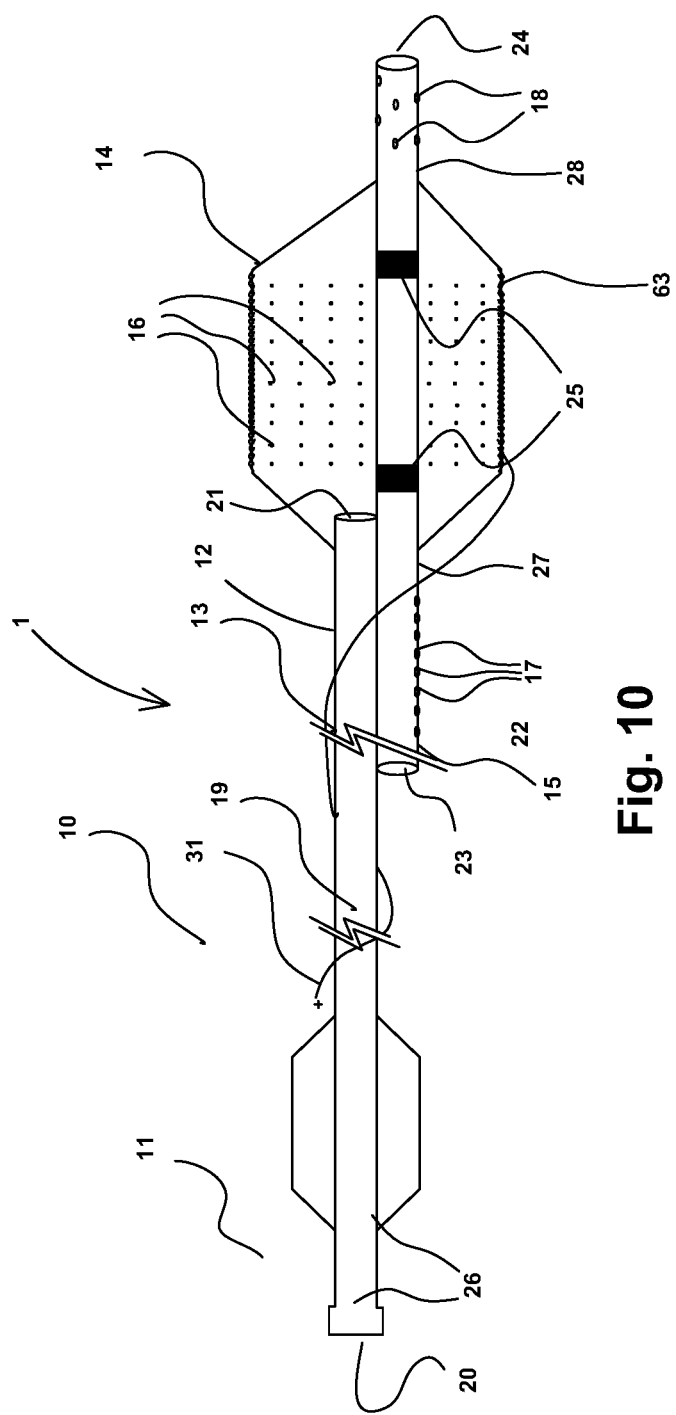
FIG. 10 illustrates a side view of another non-limiting exemplary embodiment of the medical device that includes an expandable balloon and a bypass passageway in accordance with the present disclosure.

Referring now to FIG. 10, the medical device is similar to the medical device previously discussed with respect to FIG. 1. However, the medical device 1 includes a stent 60 mounted to the outside of the inflatable balloon 14. When a stent 60 is used, a wire 31 can optionally be releasably positioned in the struts of the stent such that the stent 60 can function as an electrode to facilitate electroporation and/or iontophoresis. When the stent 60 is expanded, wire 31 can remain in contact with the stent 60. Once the inflatable balloon 14 is removed from the treatment site, the wire 31 can also be disconnected from the stent 60 while the expanded stent 60 remains at the treatment site in the blood vessel. As can be appreciated, the stent can be substituted for an electrode that is mounted on the outside of the inflatable balloon. As also can be appreciated, reference number 60 can represent a therapeutic agent coating on the outer surface of the outer surface of the inflatable balloon 14 instead of a stent. In such an arrangement, wire 31 is not used.

The medical device 1 of FIG. 10 can optionally include one or more radiopaque marker bands (not shown).

The medical device 1 of FIG. 10 can optionally include one or more electrodes (not shown) that are located inside the inflatable balloon and/or are at a location that is distal or proximal to the inflatable balloon 14.

Figure 14:
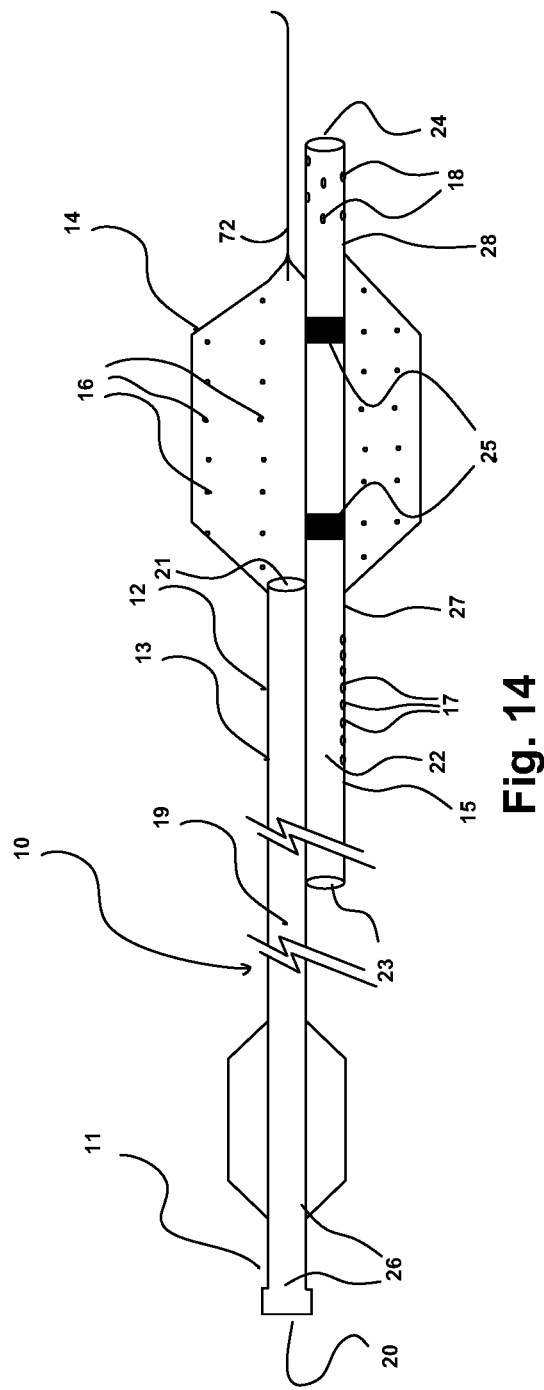
FIG. 14 illustrates a side view of another non-limiting exemplary embodiment of the medical device that includes an expandable balloon and a bypass passageway in accordance with the present disclosure.

Referring now to FIG. 14, another non-limiting medical device 1 is illustrated. The medical device is similar to the medical device previously discussed with respect to FIG. 1. However, there is provided a guide wire exit port 70 that is located distal to the inflatable balloon 14. In such an arrangement, the guide wire is outside the inflatable balloon and is positioned between the inflatable balloon 14 and the blood vessel wall BV when the inflatable balloon 14 is inflated.

Figure 13:
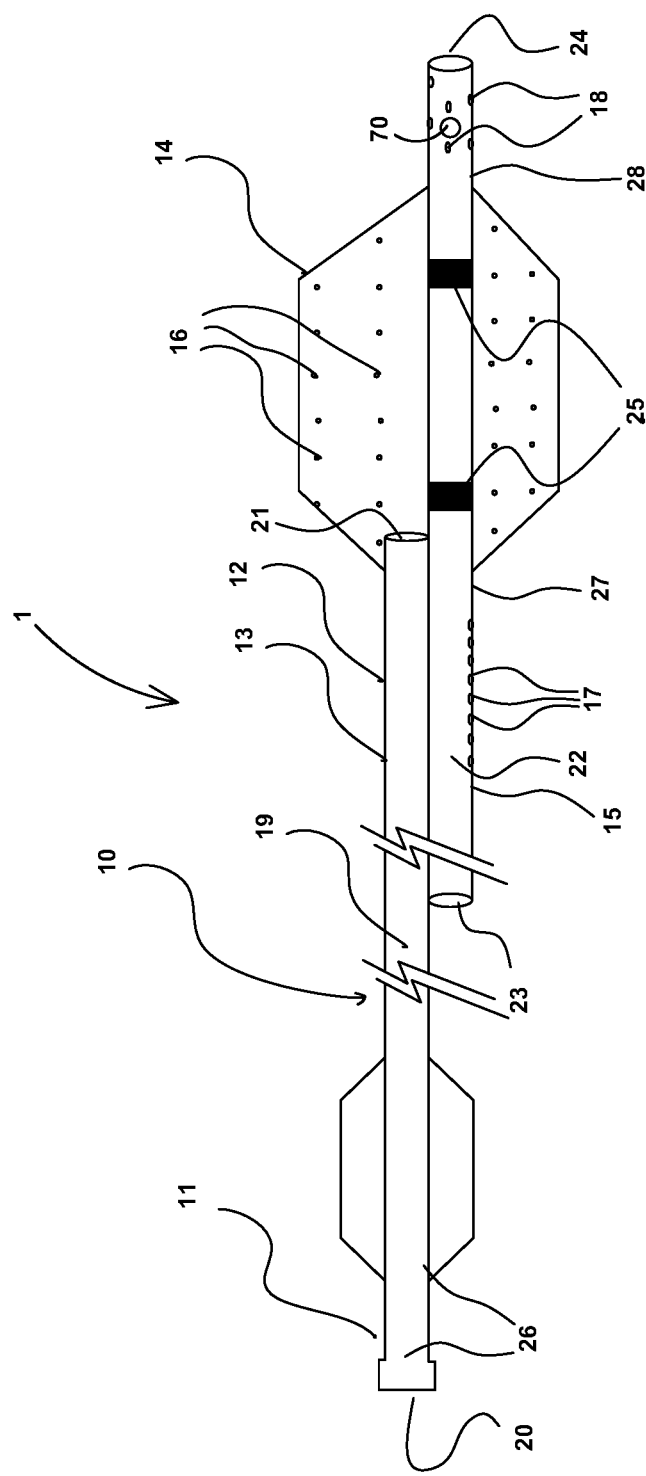
FIG. 13 illustrates a side view of another non-limiting exemplary embodiment of the medical device that includes an expandable balloon and a bypass passageway in accordance with the present disclosure.

The medical device 1 of FIG. 13 can optionally include a stent (not shown) mounted to the outer surface of inflatable balloon 14. During inflation of the inflatable balloon 16, the stent can be caused to expand at the treatment site in the blood vessel. The stent can be optionally coated with a therapeutic agent.

The medical device 1 of FIG. 13 can optionally include a therapeutic agent coating (not shown) coated on the outer surface of inflatable balloon 14.

The medical device 1 of FIG. 13 can optionally include one or more electrodes (not shown) that are located inside the inflatable balloon and/or at a location that is distal or proximal to the inflatable balloon 14.

Referring now to FIG. 14, another non-limiting medical device 1 is illustrated. The medical device is similar to the medical device previously discussed with respect to FIG. 1. However, the distal end of the inflatable balloon 14 is configured to enable a guidewire 72 to fully pass though inflatable balloon such that the passageway 19 of the elongated body 13 of the catheter body 10 functions both as the passageway for the guidewire 72, but also enables fluid to inflate the inflatable balloon 14. The distal end of the inflatable balloon 14 can be configured to allow the guidewire 72 to pass through the distal end but minimize fluid flow through the distal end. A separate guide wire is not required during the procedure while using this arrangement. In this configuration, the guidewire body 15 is no longer used with the guidewire and is only used as a bypass passageway. As such, the length of the guidewire body 15 functions solely as a bypass passageway and can optionally be much shorter such that the proximal end 23 of the guidewire body 15 can extend less than 5 inches from the proximal end 27 of the inflatable balloon 14 and the distal end 24 of the guidewire body 15 can extend less than 5 inches from the distal end 28 of the inflatable balloon 14, and typically, the proximal end 23 of the guidewire body 15 can extend less than 3 inches from the proximal end 27 of the inflatable balloon 14 and the distal end 24 of the guidewire body 15 can extend less than 2 inches from the distal end 28 of the inflatable balloon 14.

The medical device 1 of FIG. 14 can optionally include a stent (not shown) mounted to the outer surface of inflatable balloon 14. During inflation of the inflatable balloon 16, the stent can be caused to expand at the treatment site in the blood vessel. The stent can be optionally coated with a therapeutic agent.

The medical device 1 of FIG. 14 can optionally include a therapeutic agent coating (not shown) coated on the outer surface of inflatable balloon 14.

The medical device 1 of FIG. 14 can optionally include one or more electrodes (not shown) that are located inside the inflatable balloon and/or at a location that is distal or proximal to the inflatable balloon 14.

First Method of Use

The medical device 1 in accordance with the present disclosure can be used in the treatment of diseased blood vessel. As is well known in an angioplasty procedure, a bodily puncture is initially made in the arterial or venous system of the patient. A guide catheter is navigated close to the site of treatment in the blood vessel and a guidewire is navigated across the site of treatment in the blood vessel. The medical device in accordance with the present disclosure is then passed over the guidewire and placed at the site of treatment. The placement of the medical device 1 at the proper location in the blood vessel can optionally be facilitated with the use of radiopaque markers 25 on the medical device 1.

Once the medical device 1 is located at the treatment site, the inflatable balloon 14 is inflated by a fluid. The fluid may or may not include a therapeutic agent. While the inflatable balloon is inflated in the blood vessel, blood flow across the inflated balloon will not be terminated due to the bypass passageway in the medical device, thus allowing the practitioner to inflate the inflatable balloon for extended periods of time, and multiple times if needed. Such a feature of the medical device is one of the novel features of the medical device in accordance with the present invention. In prior angioplasty procedures, blood flow in the blood vessel was blocked by the inflation of the inflatable balloon; thus, the inflatable balloon could only be inflated for a few seconds (procedures in the brain), and typically no longer than 10-30 seconds without risk of damage to tissue downstream from the inflated inflatable balloon. The novel use of a bypass passageway in the medical device 1 in accordance with the present disclosure overcomes this limitation of past inflatable balloon devices. The medical device 1 can be inserted at a treatment site TS and the inflatable balloon 14 can be inflated at the treatment site for time periods much greater than 30 seconds (e.g., 40 seconds to 10+ minutes and all values and ranges therebetween) without risk of damage to tissue downstream from the inflated inflatable balloon 14. As can be appreciated, the medical device 1 can be configured such that the bypass passageway allows for sufficient quantities of blood to bypass the inflated inflatable balloon 14 so the medical device could remain in the blood vessel while the inflatable balloon is inflated for period exceeding 10 minutes without risk of damage to tissue downstream from the inflated inflatable balloon 14. As such, longer treatment times are now possible to allow the desired amount of therapeutic agent to migrate into the tissue of the wall of the blood vessel at the treatment site. The inflatable balloon 14 can be expanded for longer periods of time to properly treat the treatment site TS in the blood vessel. Longer periods of time can be used to analyze the treatment site TS while the inflatable balloon 14 is inflated. As such, the ability of the medical device to safety remain in a blood vessel while the inflatable balloon 14 is inflated for greater than 30 seconds without risk of damage to tissue downstream from the inflated inflatable balloon 14 is a significant advancement in angioplasty devices and procedures. As such, the medical device 1 in accordance with the present disclosure can be used in angioplasty procedures in neural blood vessels without risk of damage to tissue downstream while the inflatable balloon 14 is inflated for a period of time that exceeds 10 seconds (e.g., 11 seconds to 2 minutes and all values and ranges therebetween), 30 seconds, 60 seconds, and more. Such long inflation times for the inflatable balloon were not possible in neural blood vessels using prior art angioplasty devices. Likewise, the medical device 1 in accordance with the present disclosure can be used in angioplasty procedures involving myocardial infarction without risk of damage to tissue downstream while the inflatable balloon 14 is inflated for a period of time that exceeds 10 seconds (e.g., 11 seconds to 2 minutes and all values and ranges therebetween), 30 seconds, 60 seconds, and more. Furthermore, even in angioplasty procedures that allowed for the inflation of the inflatable balloon for up to about 30 seconds, the medical device 1 in accordance with the present disclosure can be used in such procedures for longer periods of time without risk of damage to tissue downstream while the inflatable balloon 14 is inflated.

The inflatable balloon 14 is generally inflated to internal pressures of 2-20 Atm. to cause the size of the passageway in the treatment area to be opened. Generally, the inflatable balloon 14 is expanded at a pressure that is sufficient to cause the cross-sectional size of the passageway in the treatment area of the blood vessel to be ±10% of the cross-sectional size of the passageway of the blood vessel at a location that proximal (e.g., within 1-3 cm of the proximal end of the treatment area) and/or distal (e.g., within 1-3 cm. of the distal end of the treatment area) to the treatment area of the blood vessel. If after a first treatment of the treatment site by the inflatable balloon 14, the cross-sectional size of the passageway in the treatment area of the blood vessel is less than 100% of the cross-sectional size of the passageway of the blood vessel at a location that proximal and/or distal to the treatment area of the blood vessel, the inflatable balloon 14 can be re-inflated at the treatment site one or more times to achieve the desired cross-sectional size of the passageway in the treatment area of the blood vessel.

Once the treatment at the treatment site is complete, the inflatable balloon 14 (with the guidewire, catheter body, etc.) is partially or fully deflated and removed from the blood vessel.

First Optional Additional Treatment for First Method of Use

The medical device 1 optionally includes a stent positioned about the outer surface of the inflatable balloon 14 The stent is caused to expand at the treatment site when the inflatable balloon is inflated. The expanded stent typically remains at the treatment site when the inflatable balloon is at least partially deflated and removed from the treatment site.

Second Optional Treatment for First Method of Use

A therapeutic agent can optionally be introduced by the medical device 1 such the therapeutic agent can be used to treat the blood vessel at the treatment site. The amount of dose for a therapeutic material needed for each patient is generally pre-determined by the practitioner.

In one non-limiting arrangement, the outer surface of the inflatable balloon 14 can optionally be coated with one or more therapeutic agents. As such, when the inflatable balloon 14 is inflated at the treatment site, the therapeutic agent on the outer surface of the inflatable balloon 14 can contact the treatment area of the blood vessel. Generally, the therapeutic agent enters the tissue of the blood vessel; however, this is not required.

In another non-limiting arrangement, when the medical device 1 optionally includes a stent, the stent optionally can be coated with one or more therapeutic agents. As such, when the inflatable balloon 14 is inflated and causes the stent to expand and contact the inner wall of the treatment area, the therapeutic agent on the stent can contact the treatment area of the blood vessel. Generally, the therapeutic agent enters the tissue of the blood vessel; however, this is not required.

In another non-limiting arrangement, the inflatable balloon 14 optionally includes balloon wall openings 16. When the inflatable balloon 14 is inflated by a fluid that includes a therapeutic agent, the therapeutic agent will flow from the interior of the inflatable balloon 14, through the one or more balloon wall openings 16, and contact the treatment area of the blood vessel. Generally, the therapeutic agent enters the tissue of the blood vessel; however, this is not required. When the inflatable balloon includes a coating of therapeutic material and/or the stent (when used) includes a therapeutic coating, the inflatable balloon is optionally absent the one or more balloon wall openings 16.

Figure 12:
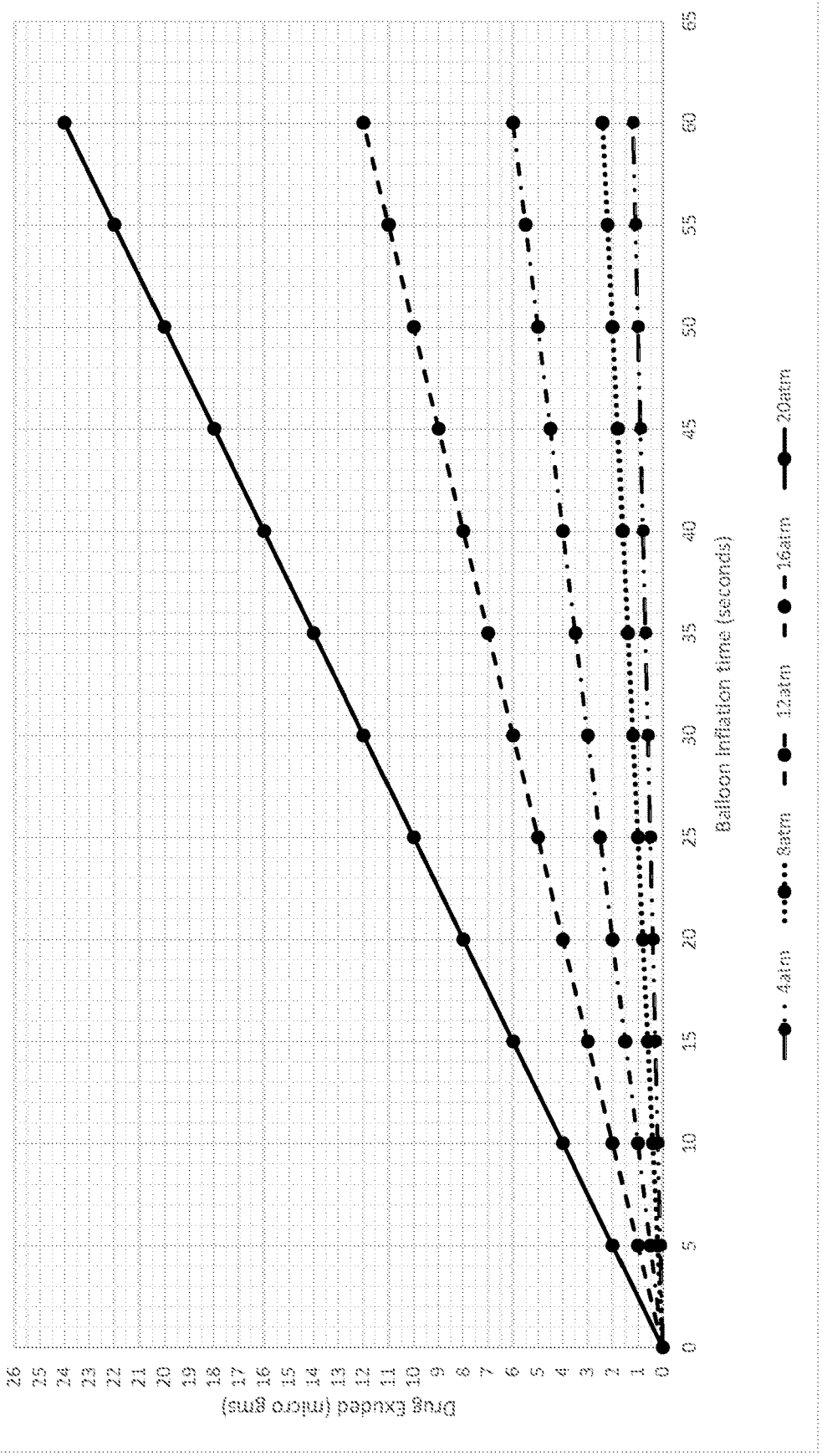
FIG. 12 is a graph illustrating the amount of therapeutic drug that is extruded from an inflatable balloon over time as a function of internal pressure in the inflatable balloon.

The pressure applied on the fluid in the inflatable balloon 14 and the time for which the pressure is applied will dictate the amount of therapeutic material that flows through the one or more balloon wall openings 16. An example of the dose at different pressures in given in FIG. 12. In FIG. 12, the amount of therapeutic agent through the wall of the inflatable balloon 14 is indicated against the time duration for which the fluid is held under pressure. FIG. 12 also indicates the amount of therapeutic agent flowing across the wall of the inflatable balloon 14 when held under various pressures. The amount of therapeutic agent flowing across the wall of the inflatable balloon 14 also depends upon the pore size, pore density, total number of pores, the concentration of the therapeutic agent, and the viscosity. The typical balloon wall opening size in the inflatable balloon 14 used for treatment of coronary artery is 0.05-5 microns (and all values and ranges therebetween) with a balloon wall opening density of 1-25 holes per square centimeter (and all values and ranges therebetween). For example, a 0.1 wt. % solution of therapeutic agent in a saline solution has a viscosity of 2 cps at 77° F. under 8 Atm. pressure inside the inflatable balloon 14 wherein the hole density of 25 holes per $cm^2$, about 0.6 micrograms of therapeutic agent will pass through the wall of the inflatable balloon per square centimeter of the inflatable balloon in 15 seconds. For larger balloon wall opening sizes of 5-15 microns, the balloon wall opening density is about 1-10 holes per square centimeter. As is illustrated in FIG. 12, higher internal pressure of the inflatable balloon 14 will result in larger quantities of therapeutic agent as a function of time to flow through the balloon wall openings 16 and into the tissue of the blood vessel wall BV.

Once the delivery of the therapeutic material is complete (e.g., therapeutic coating on inflatable balloon, therapeutic coating on stent, and/or therapeutic flowing through one or more balloon wall openings), the inflatable balloon 14 is optionally deflated to allow the practitioner a chance to evaluate the extent of treatment of the expansion of the narrowed passageway of the diseased blood vessel. As stated, above, the inflatable balloon 14 can be inflated multiple times in the treatment site to achieve the desired cross-sectional size of the passageway in the treatment area of the blood vessel. Once the treatment at the treatment site is complete, the inflatable balloon 14 is partially or fully deflated and removed from the blood vessel also with the guidewire, catheter body, etc.

Third Optional Treatment for First Method of Use

When a therapeutic agent is to be applied to the treatment site, the medical device 1 can optionally include one or more electrodes. Such optional electrodes can be energized when the inflatable balloon 14 is inflated to provide a current to the blood vessel wall BV so as to facilitate therapeutic material absorption and/or migration into the blood vessel wall BV using electroporation and/or iontophoresis.

The one or more electrodes can be located a) inside the inflatable balloon, b) outside the inflatable balloon, c) the stent (when used) that is mounted on the outer surface of the inflatable balloon, and/or d) on or above the surface of the patient's body and in close proximity to another electrode on the medical device or stent.

Second Method of Use

The second novel method in accordance with the present disclosure can be used with the First Method of Use described above or can be an independent method of use. The second novel method in accordance with the present disclosure involves the use of different viscosity fluids to inflate an inflatable balloon 14 that includes one or more balloon wall openings 16.

In an angioplasty procedure, a bodily puncture is initially made in the arterial or venous system of the patient. A guide catheter is then navigated close to the site of treatment in the blood vessel and a guidewire is navigated across the site of treatment in the blood vessel. The medical device in accordance with the present disclosure is then passed over the guidewire and placed at the site of treatment. The placement of the medical device 1 at the proper location in the blood vessel can optionally be facilitated with the use of radiopaque markers 25 on the medical device 1.

Once the medical device 1 is located at the treatment site, the inflatable balloon 14 is inflated by a fluid. The fluid may or may not include a therapeutic agent. The inflatable balloon 14 includes balloon wall openings 16. When the inflatable balloon 14 is inflated by a fluid that includes a therapeutic agent, the therapeutic agent will flow from the interior of the inflatable balloon 14, through the one or more balloon wall openings 16, and contact the treatment area of the blood vessel. Generally, the therapeutic agent enters the tissue of the blood vessel; however, this is not required. The pressure applied on the fluid in the inflatable balloon 14 and the time for which the pressure is applied will dictate the amount of fluid that flows through the one or more balloon wall openings 16.

When the inflatable balloon 14 includes one or more balloon wall openings 16, the maximum internal pressure obtainable in the inflatable balloon is generally no more than 8 Atm. In some angioplasty procedure, inflation pressures of up to 8 Atm. will be sufficient to cause the cross-sectional size of the passageway in the treatment area of the blood vessel to be ±10% of the cross-sectional size of the passageway of the blood at a location proximal (e.g., within 1-3 cm. of the proximal end of the treatment area) and/or distal (e.g., within 1-3 cm. of the distal end of the treatment area) to the treatment area of the blood vessel. However, for some treatment sites, inflation pressures of greater than 8 Atm. are required to cause the cross-sectional size of the passageway in the treatment area of the blood vessel to be ±10% of the cross-sectional size of the passageway of the blood at a location proximal and/or distal to the treatment area of the blood vessel. As such, if after the first inflation of the inflatable balloon (and possibly after additional inflations of the inflatable balloon using a non-high viscous solution) it is determined that opening in the blood vessel at the treatment site has not been sufficient opened, higher inflation pressures are achieved by the use of a high viscous solution.

The high viscosity fluid includes particles having a size that cannot pass through or do not easily pass through the one or more balloon wall openings such that the inflation pressure in the inflatable balloon can be increased even though the inflatable balloon includes balloon wall openings. For example, when a non-high viscosity fluid is used to inflate the inflatable balloon (e.g., a solution that includes a therapeutic agent that has a viscosity of about 2 cps at 77° F. and wherein the particle size in the solution is less than 50% of the size of the openings of the balloon wall openings when the inflatable balloon is inflated), the maximum internal inflation pressure in the inflatable balloon is about 4-8 Atm. When a high viscosity fluid is used to inflate the inflatable balloon (e.g., a solution that has a viscosity of 2.5 or greater cps at 77° F. and wherein the particle size in the solution is greater than 100% of the size of the openings of the balloon wall openings when the inflatable balloon is inflated), the inflatable balloon can be inflated by internal inflation pressures exceeding 8 Atm. (e.g., 10-20 Atm.).

Once the treatment at the treatment site is complete, the inflatable balloon 14 is partially or fully deflated and removed from the blood vessel, along with the guidewire, catheter body, etc.

First Optional Additional Treatment for Second Method of Use

The medical device 1 can optionally include a bypass passageway to allow blood to flow past the medical device 1 while the inflatable balloon 14 is inflated, thus allowing the practitioner to inflate the inflatable balloon for extended periods of time.

Second Optional Additional Treatment for Second Method of Use

The medical device 1 optionally includes a stent positioned about the outer surface of the inflatable balloon 14. The stent is caused to expand at the treatment site when the inflatable balloon is inflated. The expanded stent typically remains at the treatment site when the inflatable balloon is at least partially deflated and removed from the treatment site.

The stent optionally can be coated with one or more therapeutic agents. As such, when the inflatable balloon 14 is inflated and causes the stent to expand and contact the inner wall of the treatment area, the therapeutic agent on the stent can contact the treatment area of the blood vessel. Generally, the therapeutic agent enters the tissue of the blood vessel; however, this is not required.

Third Optional Treatment for Second Method of Use

The outer surface of the inflatable balloon 14 can optionally be coated with one or more therapeutic agents. As such, when the inflatable balloon 14 is inflated at the treatment site, the therapeutic agent on the outer surface of the inflatable balloon 14 can contact the treatment area of the blood vessel. Generally, the therapeutic agent enters the tissue of the blood vessel; however, this is not required.

Fourth Optional Treatment for Second Method of Use

When a therapeutic agent is applied to the treatment site, the medical device 1 can optionally include one or more electrodes. Such optional electrodes can be energized when the inflatable balloon 14 is inflated to provide a current to the blood vessel wall BV to facilitate therapeutic material absorption and/or migration into the blood vessel wall BV using electroporation and/or iontophoresis.

The one or more electrodes can be located a) inside the inflatable balloon, b) outside the inflatable balloon, c) on the stent (when used) that is mounted on the outer surface of the inflatable balloon, and/or d) on or above the surface of the patient's body and in close proximity to another electrode on the medical device or stent.

Third Method of Use

The third novel method in accordance with the present disclosure can be used with the First and/or Second Method of Use described above or can be an independent method of use. The third novel method in accordance with the present disclosure involves the use of different current treatment levels and current treatment times to improve the migration of therapeutic agent into the tissue of the blood vessel.

In an angioplasty procedure, a bodily puncture is initially made in the arterial or venous system of the patient. A guide catheter is then navigated close to the site of treatment in the blood vessel and a guidewire is navigated across the site of treatment in the blood vessel. The medical device in accordance with the present disclosure is passed over the guidewire and placed at the site of treatment. The placement of the medical device 1 at the proper location in the blood vessel can optionally be facilitated with the use of radiopaque markers 25 on the medical device 1.

Once the medical device 1 is located at the treatment site, the inflatable balloon 14 is inflated by a fluid. A therapeutic agent is introduced at the treatment site by the medical device 1 such that the therapeutic agent can be used to treat the blood vessel at the treatment site. The dosage of a therapeutic material needed for each patient is generally pre-determined by the practitioner.

In one non-limiting arrangement, the outer surface of the inflatable balloon 14 can optionally be coated with one or more therapeutic agents. As such, when the inflatable balloon 14 is inflated at the treatment site, the therapeutic agent on the outer surface of the inflatable balloon 14 can contact the treatment area of the blood vessel.

In another non-limiting arrangement, when the medical device 1 optionally includes a stent, the stent optionally can be coated with one or more therapeutic agents. As such, when the inflatable balloon 14 is inflated and causes the stent to expand and contact the inner wall of the treatment area, the therapeutic agent on the stent can contact the treatment area of the blood vessel.

In another non-limiting arrangement, the inflatable balloon 14 optionally includes balloon wall openings 16. When the inflatable balloon 14 is inflated by a fluid that includes a therapeutic agent, the therapeutic agent flows from the interior of the inflatable balloon 14, through the one or more balloon wall openings 16, and contacts the treatment area of the blood vessel.

The medical device 1 includes one or more electrodes to provide a current to the blood vessel wall BV to facilitate therapeutic material absorption and/or migration into the blood vessel wall BV using electroporation and iontophoresis. The one or more electrodes can be located a) inside the inflatable balloon, b) outside the inflatable balloon, c) on the stent (when used) that is mounted on the outer surface of the inflatable balloon, and/or d) on or above the surface of the patient's body and in close proximity to another electrode on the medical device or stent.

The one or more electrodes are energized with a current to promote migration of the therapeutic agent into the blood vessel by iontophoresis. Iontophoresis occurs while the therapeutic agent is being transferred from the medical device to the blood vessel.

Once transfer of the therapeutic agent from the medical device to the blood vessel is complete, the one or more electrodes can be energized at a different level to promote further migration of the therapeutic agent into the blood vessel by electroporosis.

To improve the uptake of the therapeutic agent an electrical field is applied across the cells at the site of treatment without causing damage to the normal cells. The strength of the current applied determines whether the type of treatment is iontophoresis or electroporosis. Iontophoresis is the process by which the electric field increases the permeability of the tissue to absorb therapeutic agent. In order to enhance the uptake of the therapeutic agent deep into the walls of the blood vessel, a mild electrical voltage ranging from 0.1V to 15V (and all values and ranges therebetween) at a current of 0.1-12 mA/cm$^2$ (and all values and ranges therebetween) is applied between the two electrodes, and typically 0.1V-15V at 0.3-0.6 mA/cm$^2$.

In accordance with the present disclosure, the therapeutic agent is first introduced into the blood vessel walls by methods discussed above. During the inflation of the inflatable balloon and delivery of the therapeutic agent, a current is applied to one or more electrodes causing iontophoresis. If one of the electrodes is outside the balloon cavity (as shown in FIGS. 3A, 3B, 3C, 4, 7, 15B), the electrode in direct contact with balloon cavity or closest to the balloon cavity is the cathode. The simultaneous blood flow through the bypass passageway allows prolonged treatment without affecting the downstream tissues or organs. The use of iontophoresis facilitates in ensuring the penetration of the therapeutic agent deep within the walls of the blood vessel at the treatment site, but may not necessarily cause the penetration of the therapeutic agent into the cell walls of the cells that form the blood vessel wall.

Once the tissue of the diseased vessel is partially or fully saturated with the therapeutic agent, a high voltage can optionally be applied to the one or more electrodes in one or more short pulses to cause electroporation. Electroporation is a process by which the cell membrane is made permeable for a short duration to allow large molecules to enter the cell. During electroporation, the electrodes are energized at 0.1 kV-500 kV (kilovolt) (and all values and ranges therebetween) and the pulse length (pulse duration) is 0.3-99 microseconds (and all values and ranges therebetween). In one non-limiting arrangement, 200-2000 V/cm (and all values and ranges therebetween) are used for the electroporation process. As can be appreciated, a longer pulse at lower voltage can be applied to the one or more electrodes for effective electroporation without damaging the cells in the blood vessel wall. The number of pulses can be 1-50 pulses (and all values and ranges therebetween) and the time period between the pulses can be 0.1 milliseconds to 10 seconds (and all values and ranges therebetween).

In one non-limiting arrangement, an electroporation process is optionally used after an iontophoresis when 1) the blood vessel wall at the treatment site is saturated with therapeutic agent, 2) the flow of therapeutic agent through the one or more balloon wall openings has been terminated at the treatment site, or the flow of therapeutic agent has been reduced to less than 20% of the maximum flow rate through the balloon wall openings at the treatment site, and/or 3) no further coating of therapeutic agent exists on the outer surface of the inflatable balloon.

In another non-limiting arrangement, only an iontophoresis process is used.

In another non-limiting arrangement, only an electroporation process is used.

In another non-limiting arrangement, only an iontophoresis process is used after an electroporation process.

Once the delivery of the therapeutic material into the blood vessel is complete, and the iontophoresis process or iontophoresis and electroporation processes are completed, the inflatable balloon 14 is optionally deflated to allow the practitioner a chance to evaluate the extent of treatment of the expansion of the narrowed passageway of the diseased blood vessel. As stated above, the inflatable balloon 14 can be inflated multiple times in the treatment site to achieve the desired cross-sectional size of the passageway in the treatment area of the blood vessel.

Once the treatment at the treatment site is complete, the inflatable balloon 14 is partially or fully deflated and removed from the blood vessel also with the guidewire, catheter body, etc.

First Optional Additional Treatment for Third Method of Use

The medical device 1 can optionally include a bypass passageway to allow blood to flow past the medical device 1 while the inflatable balloon 14 is inflated, thus allowing the practitioner to inflate the inflatable balloon for extended periods of time.

Second Optional Additional Treatment for Third Method of Use

The medical device 1 optionally includes a stent positioned about the outer surface of the inflatable balloon 14. The stent is caused to expand at the treatment site when the inflatable balloon is inflated. The expanded stent typically remains at the treatment site when the inflatable balloon is at least partially deflated and removed from the treatment site.

The stent optionally can be coated with one or more therapeutic agents. As such, when the inflatable balloon 14 is inflated and causes the stent to expand and contact the inner wall of the treatment area, the therapeutic agent on the stent can contact the treatment area of the blood vessel. Generally, the therapeutic agent enters the tissue of the blood vessel; however, this is not required.

Third Optional Treatment for Third Method of Use

A high viscosity fluid can be used to inflate the inflatable balloon as described above with regard to the Second Method of Use.

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall there between. The disclosure has been described with reference to the preferred embodiments. These and other modifications of the preferred embodiments as well as other embodiments of the disclosure will be obvious from the disclosure herein, whereby the foregoing descriptive matter is to be interpreted merely as illustrative of the disclosure and not as a limitation. It is intended to include all such modifications and alterations insofar as they come within the scope of the appended claims.

What is claimed:

1. A medical device comprising a catheter, a first inflatable balloon mounted on said catheter, and a bypass passageway that enables continued blood flow in a blood vessel and about said first inflatable balloon when said first inflatable balloon is inflated in the blood vessel; said bypass passageway includes one or more arrangements selected from the group consisting of a) said bypass passageway is at least partially formed of a fluid passageway that is separate from said catheter, b) said bypass passageway includes a fluid passageway that extends beyond said catheter, c) said bypass passageway includes a proximal end opening and one or more proximal side wall openings that are both positioned proximal to said first inflatable balloon and wherein said proximal end opening and said one or more proximal side openings enable blood flow into an interior of said bypass passageway when said first inflatable balloon is inflated in the blood vessel, d) said bypass passageway includes a distal end opening and one or more distal side wall openings that are both positioned distal to said first inflatable balloon and wherein said distal end opening and said one or more distal side openings enable blood flow to exit from an interior of said bypass passageway when said first inflatable balloon is inflated in the blood vessel, and e) said bypass passageway includes a first electrode or electrically conductive element positioned on said bypass passageway, said first electrode or electrically conductive element is electrically connected via a wire to a power source spaced rearwardly of a proximal end of said first inflatable balloon.

2. The medical device as defined in claim 1, wherein said first inflatable balloon includes one or more balloon wall openings.

3. The medical device as define in claim 2, wherein said one or more balloon wall openings has a size of 0.1-25 microns.

4. The medical device as defined in claim 1, wherein said catheter has a passageway having an opening in an interior of said first inflatable balloon; a distal portion of said catheter is connected to a proximal portion of said first inflatable balloon.

5. The medical device as defined in claim 1, wherein said bypass passageway is partially or fully formed by one or more structures selected from the group consisting of a) said catheter, b) a guidewire passageway, and c) a passageway separate from said catheter and said guidewire passageway.

6. The medical device as defined in claim 1, wherein said bypass passageway has a proximal end that is spaced rearwardly of a proximal end of said first inflatable balloon; said bypass passageway has a distal end that is spaced forwardly of a distal end of said first inflatable balloon; said proximal end includes said proximal end opening, said distal end includes said distal end opening.

7. The medical device as defined in claim 1, wherein said bypass passageway includes one or more arrangements selected from the group consisting of a) said proximal end opening is located within 20 inches of a proximal end of said first inflatable balloon, b) said one or more proximal side openings are located within 20 inches of a proximal end of said first inflatable balloon, c) said distal end opening is located within 5 inches of a distal end of said first inflatable balloon, and d) said one or more distal side openings are located within 5 inches of a distal end of said first inflatable balloon.

8. The medical device as defined in claim 1, further including one or more luer connectors on said catheter.

9. The medical device as defined in claim 1, further including a first electrode or electrically conductive element; said first electrode or electrically conductive element is electrically connected via a wire to a power source spaced rearwardly of a proximal end of said first inflatable balloon; said first electrode or electrically conductive element is located in one or more locations selected from the group consisting of a) inside said first inflatable balloon, b) on an exterior surface of said first inflatable balloon, c) spaced rearwardly of a proximal end of said first inflatable balloon, d) spaced forwardly of a distal end of said first inflatable balloon, e) positioned on said bypass passageway, and f) positioned on said catheter.

10. The medical device as defined in claim 9, further including a second electrode or electrically conductive element; said second electrode or electrically conductive element is located in one or more locations selected from the group consisting of a) inside said first inflatable balloon, b) on an exterior surface of said first inflatable balloon, c) spaced rearwardly of a proximal end of said first inflatable balloon, d) spaced forwardly of a distal end of said first inflatable balloon, e) spaced outside of said blood vessel, f) spaced outside the body and positioned close to or in contact with the body, g) positioned on said bypass passageway, and h) positioned on said catheter; said second electrode or electrically conductive element is spaced from said first electrode or electrically conductive element.

11. The medical device as defined in claim 1, further including a first radiopaque marker; said first radiopaque marker is located in one or more locations selected from the group consisting of a) inside said first inflatable balloon, b) on an exterior surface of said first inflatable balloon, c) spaced rearwardly of a proximal end of said first inflatable balloon, d) spaced forwardly of a distal end of said first inflatable balloon, e) positioned on said bypass passageway, and f) positioned on said catheter.

12. A method for treating a blood vessel comprising:
providing a medical device; said medical device comprised of a catheter, a first inflatable balloon mounted on said catheter, and a bypass passageway; said bypass passageway includes one or more arrangements selected from the group consisting of a) said bypass passageway is at least partially formed of a fluid passageway that is separate from said catheter, b) said bypass passageway includes a fluid passageway that extends beyond said catheter, c) said bypass passageway includes a proximal end opening and one or more proximal side wall openings that are both positioned proximal to said first inflatable balloon and wherein said proximal end opening and said one or more proximal side openings enable blood flow into an interior of said bypass passageway when said first inflatable balloon is inflated in the blood vessel, d) said bypass passageway includes a distal end opening and one or more distal side wall openings that are both positioned distal to said first inflatable balloon and wherein said distal end opening and said one or more distal side openings enable blood flow to exit from an interior of said bypass passageway when said first inflatable balloon is inflated in the blood vessel, and e) said bypass passageway includes a first electrode or electrically conductive element positioned on said bypass passageway, said first electrode or electrically conductive element is electrically connected via a wire to a power source spaced rearwardly of a proximal end of said first inflatable balloon;

inserting said medical device into said blood vessel;

positioning said medical device at a treatment site in said blood vessel; and, inflating said first inflatable balloon at said treatment site;

wherein said bypass passageway is configured to enable continued blood flow in said blood vessel and about said first inflatable balloon when said first inflatable balloon is inflated in said blood vessel.

13. The method as defined in claim 12, wherein said step of inflating includes inserting pressurized fluid into an interior of said first inflatable balloon; said pressurized fluid includes one or more materials selected from the group consisting of water, blood, blood plasma, saline solution, therapeutic agent, contrast agent, and radiopaque agent.

14. The method as defined in claim 12, wherein said first inflatable balloon includes one or more balloon wall openings; and further includes the step of inserting a therapeutic agent into said first inflatable balloon and causing said therapeutic agent to pass through said one or more balloon wall openings while said first inflatable balloon is inflated at said treatment site.

15. The method as defined in claim 14, further including the step of inserting a high viscosity solution into said first inflatable balloon; said high viscosity solution includes particles having an average particle size of 70-100+% of an average size of said one or more balloon wall openings while said first inflatable balloon is inflated.

16. The method as defined in claim 12, wherein said step of inflating includes inflating said first inflatable balloon in said blood vessel that is located in a) said brain for a period of greater than 10 seconds without damaging tissue downstream from said first inflatable balloon, or b) a heart that is causing a myocardial infarction for a period of greater than 10 seconds without damaging tissue downstream from said first inflatable balloon.

17. The method as defined in claim 12, wherein said step of inflating includes inflating said first inflatable balloon in said blood vessel for a period of over 30 seconds without damaging tissue downstream from said first inflatable balloon.

18. The method as defined in claim 12, wherein said step of inflating includes inflating said first inflatable balloon in said blood vessel for a period of over 60 seconds without damaging tissue downstream from said first inflatable balloon.

19. The method as defined in claim 12, wherein said medical device further includes a first electrode or electrically conductive element; said first electrode or electrically conductive element electrically connected via a wire to a power source spaced rearwardly of a proximal end of said first inflatable balloon; said first electrode located in one or more locations selected from the group consisting of a) inside said first inflatable balloon, b) on an exterior surface of said first inflatable balloon, c) spaced rearwardly of a proximal end of said first inflatable balloon, d) spaced forwardly of a distal end of said first inflatable balloon, e) positioned on said bypass passageway, and f) positioned on said catheter; and further including the step of energizing said first electrode to to facilitate in the migration of therapeutic agent into tissue of a wall of said blood vessel.

\* \* \* \* \*